US011266297B2

(12) United States Patent
Ubbesen et al.

(10) Patent No.: US 11,266,297 B2
(45) Date of Patent: *Mar. 8, 2022

(54) PORTABLE MEDICAL MONITOR

(71) Applicant: AMBU A/S, Ballerup (DK)

(72) Inventors: Line Sandahl Ubbesen, Holte (DK); Brian Nielsen, Næstved (DK); Henrik Frengler, Værløse (DK); Kasper Rieland Jakobsen, Roskilde (DK); Nai-Hua Chen, Kaohsiung (TW)

(73) Assignee: AMBU A/S, Ballerup (DK)

(*) Notice: Subject to any disclaimer, the term of this patent is extended or adjusted under 35 U.S.C. 154(b) by 0 days.

This patent is subject to a terminal disclaimer.

(21) Appl. No.: 17/097,739

(22) Filed: Nov. 13, 2020

(65) Prior Publication Data

US 2021/0259519 A1 Aug. 26, 2021

Related U.S. Application Data

(63) Continuation of application No. 16/904,245, filed on Jun. 17, 2020, now Pat. No. 10,835,106.

(30) Foreign Application Priority Data

Feb. 21, 2020 (DK) .......................... PA 2020 70116

(51) Int. Cl.
*A61B 1/00* (2006.01)
*A61B 1/04* (2006.01)

(52) U.S. Cl.
CPC ...... *A61B 1/00048* (2013.01); *A61B 1/00004* (2013.01); *A61B 1/00052* (2013.01); *A61B 1/04* (2013.01); *A61B 1/00045* (2013.01)

(58) Field of Classification Search
CPC .... A61B 1/04; A61B 1/00048; A61B 1/00052
See application file for complete search history.

(56) References Cited

U.S. PATENT DOCUMENTS

| 4,455,008 A | 6/1984 | MacKew |
| 5,078,615 A | 1/1992 | Benson et al. |

(Continued)

FOREIGN PATENT DOCUMENTS

| CN | 1428895 A | 7/2003 |
| CN | 1770564 A | 5/2006 |

(Continued)

OTHER PUBLICATIONS

Danish Search Report dated May 29, 2020 in Application No. PA 2020 70117.

(Continued)

*Primary Examiner* — Zhubing Ren
(74) *Attorney, Agent, or Firm* — Faegre Drinker Biddle & Reath LLP

(57) ABSTRACT

A portable monitor operable in a first orientation and a second orientation. The monitor includes a housing and a handle having arms. A back side of the housing includes grooves sized and shaped to receive, respectively, the arms of the handle. The handle is pivotable about handle axles to a plurality of positions including a first position, in which the arms are received by first sections of the grooves, a second position, in which the arms are received by second sections of the grooves, and intermediate positions between the first position and the second position.

22 Claims, 24 Drawing Sheets

(56) References Cited

U.S. PATENT DOCUMENTS

| | | | |
|---|---|---|---|
| 5,574,477 | A | 11/1996 | Shimizu et al. |
| 5,611,513 | A | 3/1997 | Rosen |
| 5,775,935 | A | 7/1998 | Barna |
| 5,873,814 | A | 2/1999 | Adair |
| 5,877,802 | A | 3/1999 | Takahashi et al. |
| 5,879,288 | A | 3/1999 | Suzuki et al. |
| 6,256,075 | B1 | 7/2001 | Yang |
| 6,339,446 | B1 | 1/2002 | Miyoshi |
| 6,381,484 | B1 | 4/2002 | Ayanruoh |
| 6,471,649 | B1 | 10/2002 | Saccardo et al. |
| 6,508,809 | B1 | 1/2003 | Bacher |
| 6,554,765 | B1 | 4/2003 | Yarush et al. |
| 6,636,254 | B1 | 10/2003 | Onishi et al. |
| 6,738,477 | B1 | 5/2004 | Kam |
| 6,950,691 | B2 | 9/2005 | Uchikubo |
| 7,338,438 | B2 | 3/2008 | Iida |
| 7,492,388 | B2 | 2/2009 | Odlivak et al. |
| 7,520,854 | B2 | 4/2009 | Sato |
| 7,659,912 | B2 | 2/2010 | Akimoto et al. |
| 7,889,227 | B2 | 2/2011 | Rahn et al. |
| 8,025,536 | B1 | 9/2011 | Kelly |
| 8,157,726 | B2 | 4/2012 | Melder |
| 8,162,823 | B2 | 4/2012 | Suzuki |
| 8,189,993 | B2 | 5/2012 | Tashiro et al. |
| 8,294,733 | B2 | 10/2012 | Eino |
| 8,439,827 | B2 | 5/2013 | Matsuura |
| 8,526,176 | B2 | 9/2013 | Clark et al. |
| 8,790,250 | B2 | 7/2014 | Petersen et al. |
| 8,808,164 | B2 | 8/2014 | Hoffman et al. |
| 8,830,308 | B2 | 9/2014 | Taniguchi |
| 8,882,662 | B2 | 11/2014 | Charles |
| 8,918,740 | B2 | 12/2014 | Nishiyama |
| 8,941,706 | B2 | 1/2015 | Guo et al. |
| 9,030,541 | B2 | 5/2015 | Kutsuma et al. |
| 9,118,818 | B2 | 8/2015 | Miyayashiki |
| 9,125,582 | B2 | 9/2015 | Petersen |
| 9,211,056 | B2 | 12/2015 | Geisser et al. |
| 9,298,351 | B2 | 3/2016 | Sato |
| 9,503,645 | B2 | 11/2016 | Ju et al. |
| 9,622,646 | B2 | 4/2017 | Ouyang et al. |
| 9,795,277 | B2 | 10/2017 | Fujita et al. |
| 9,841,280 | B2 | 12/2017 | Amling et al. |
| 9,847,002 | B2 | 12/2017 | Kiani et al. |
| 9,880,586 | B2 | 1/2018 | Ent et al. |
| 9,949,627 | B2 | 4/2018 | Oskin et al. |
| 9,993,207 | B2 | 6/2018 | Al-Ali et al. |
| 10,004,382 | B2 | 6/2018 | Umemoto |
| 10,028,649 | B2 | 7/2018 | Salvati et al. |
| 10,092,165 | B2 | 10/2018 | Power |
| 10,343,778 | B2 | 7/2019 | Peuziat |
| 10,835,106 | B1 | 11/2020 | Ubbesen et al. |
| 10,980,397 | B1 | 4/2021 | Ubbesen et al. |
| 2001/0002842 | A1 | 6/2001 | Ozawa |
| 2003/0004690 | A1* | 1/2003 | Maeda ............... G06F 1/1601 702/188 |
| 2004/0227861 | A1 | 11/2004 | Schedivy |
| 2005/0131481 | A1 | 6/2005 | Ries et al. |
| 2005/0174428 | A1 | 8/2005 | Abe |
| 2006/0049327 | A1 | 3/2006 | Chen |
| 2006/0283903 | A1 | 12/2006 | Vitito |
| 2007/0030344 | A1* | 2/2007 | Miyamoto ........... A61B 1/0669 348/65 |
| 2008/0117574 | A1 | 5/2008 | Lee |
| 2009/0109429 | A1* | 4/2009 | Scott ................. G01N 29/043 356/237.1 |
| 2009/0314915 | A1 | 12/2009 | Tu et al. |
| 2010/0245557 | A1 | 9/2010 | Luley et al. |
| 2010/0265642 | A1 | 10/2010 | Matsutani |
| 2011/0130631 | A1 | 6/2011 | Geisser et al. |
| 2011/0279993 | A1 | 11/2011 | Su |
| 2012/0130160 | A1 | 5/2012 | Borrye et al. |
| 2012/0155004 | A1 | 6/2012 | Yukawa et al. |
| 2012/0162401 | A1 | 6/2012 | Melder et al. |
| 2012/0184120 | A1 | 7/2012 | Basta et al. |
| 2012/0209123 | A1 | 8/2012 | King |
| 2013/0045135 | A1 | 2/2013 | Allen |
| 2013/0062235 | A1 | 3/2013 | Allen |
| 2013/0064709 | A1 | 3/2013 | Allen |
| 2013/0064734 | A1 | 3/2013 | Allen |
| 2014/0024891 | A1 | 1/2014 | Motoki |
| 2014/0063772 | A1 | 3/2014 | Kurachi et al. |
| 2014/0117199 | A1 | 5/2014 | Liu et al. |
| 2014/0257046 | A1 | 9/2014 | Steven |
| 2014/0316283 | A1 | 10/2014 | Kaku et al. |
| 2015/0208900 | A1 | 7/2015 | Vidas et al. |
| 2015/0362962 | A1 | 12/2015 | Lee et al. |
| 2016/0239965 | A1 | 8/2016 | Kuramoto |
| 2016/0310210 | A1 | 10/2016 | Harshman et al. |
| 2016/0331213 | A1 | 11/2016 | Kim |
| 2017/0020627 | A1 | 1/2017 | Tesar et al. |
| 2017/0102735 | A1 | 4/2017 | Blowers et al. |
| 2017/0227986 | A1 | 8/2017 | Ent et al. |
| 2017/0284457 | A1 | 10/2017 | Park |
| 2017/0360280 | A1 | 12/2017 | Levy et al. |
| 2018/0000319 | A1* | 1/2018 | Rutschmann ...... A61B 1/00048 |
| 2018/0020902 | A1 | 1/2018 | Merz et al. |
| 2018/0068437 | A1 | 3/2018 | Bronkalla et al. |
| 2018/0098684 | A1 | 4/2018 | Hagihara et al. |
| 2018/0296068 | A1 | 10/2018 | Matthison-Hansen et al. |
| 2018/0296069 | A1 | 10/2018 | Matthison-Hansen |
| 2018/0300919 | A1 | 10/2018 | Muhsin et al. |
| 2018/0303315 | A1 | 10/2018 | Matthison-Hansen |
| 2018/0303317 | A1 | 10/2018 | Matthison-Hansen |
| 2018/0303472 | A1 | 10/2018 | Matthison-Hansen et al. |
| 2018/0309908 | A1 | 10/2018 | Matthison-Hansen et al. |
| 2020/0059018 | A1 | 2/2020 | Cerniglia |

FOREIGN PATENT DOCUMENTS

| | | |
|---|---|---|
| CN | 202868218 U | 4/2013 |
| CN | 205583291 U | 9/2016 |
| CN | 107906328 A | 4/2018 |
| DE | 102016213299 A1 | 1/2018 |
| EP | 0277792 A2 | 8/1988 |
| EP | 2456290 A1 | 5/2012 |
| EP | 3123927 A1 | 2/2017 |
| GB | 2304238 A | 3/1997 |
| JP | 2010-181433 A | 8/2010 |
| JP | 2016-174836 A | 10/2016 |
| WO | 01/85020 A1 | 11/2001 |
| WO | 2013/025987 A1 | 2/2013 |
| WO | 2014/070396 A1 | 5/2014 |
| WO | 2014/142868 A1 | 9/2014 |
| WO | 2018/202268 A1 | 11/2018 |

OTHER PUBLICATIONS

International Search Report and Written Opinion in related International Application No. PCT/EP2021/053967, dated Apr. 21, 2021, 9 pages.

International Search Report and Written Opinion received for PCT Patent Application No. PCT/EP2021/053966, dated May 11, 2021, 9 pages.

International Search Report and Written Opinion received for PCT Patent Application No. PCT/EP2021/053967, dated Apr. 21, 2021, 9 pages.

International Search Report and Written Opinion received for PCT Patent Application No. PCT/EP2021/053968, dated Apr. 19, 2021, 10 pages.

International Search Report and Written Opinion received for PCT Patent Application No. PCT/EP2021/053969, dated May 19, 2021, 10 pages.

International Search Report and Written Opinion received for PCT Patent Application No. PCT/EP2021/053971, dated May 21, 2021, 9 pages.

Search Report issued in DK PA202070114, dated Jul. 17, 2020.

Search Report issued in DK PA202070115, dated Jun. 22, 2020.

Examination Report issued by the Danish Patent and Trademark Office dated Aug. 3, 2020 for Danish Application No. PA 2020 70113; 9 pages.

(56) References Cited

OTHER PUBLICATIONS

Golhar, Mayank et al. "Blood Vessel Delineation in Endoscopic Images with Deep Learning Based Scene Classification," Intelligent Virtual Agent, Berlin, pp. 147-168, Jun. 16, 2018.
International Search Report and Written opinion in related International Application No. PCT/EP2019/073483, dated Nov. 28, 2019; 5 pages.
Danish Search Report dated May 19, 2020 in Application No. PA 2020 70116.

* cited by examiner

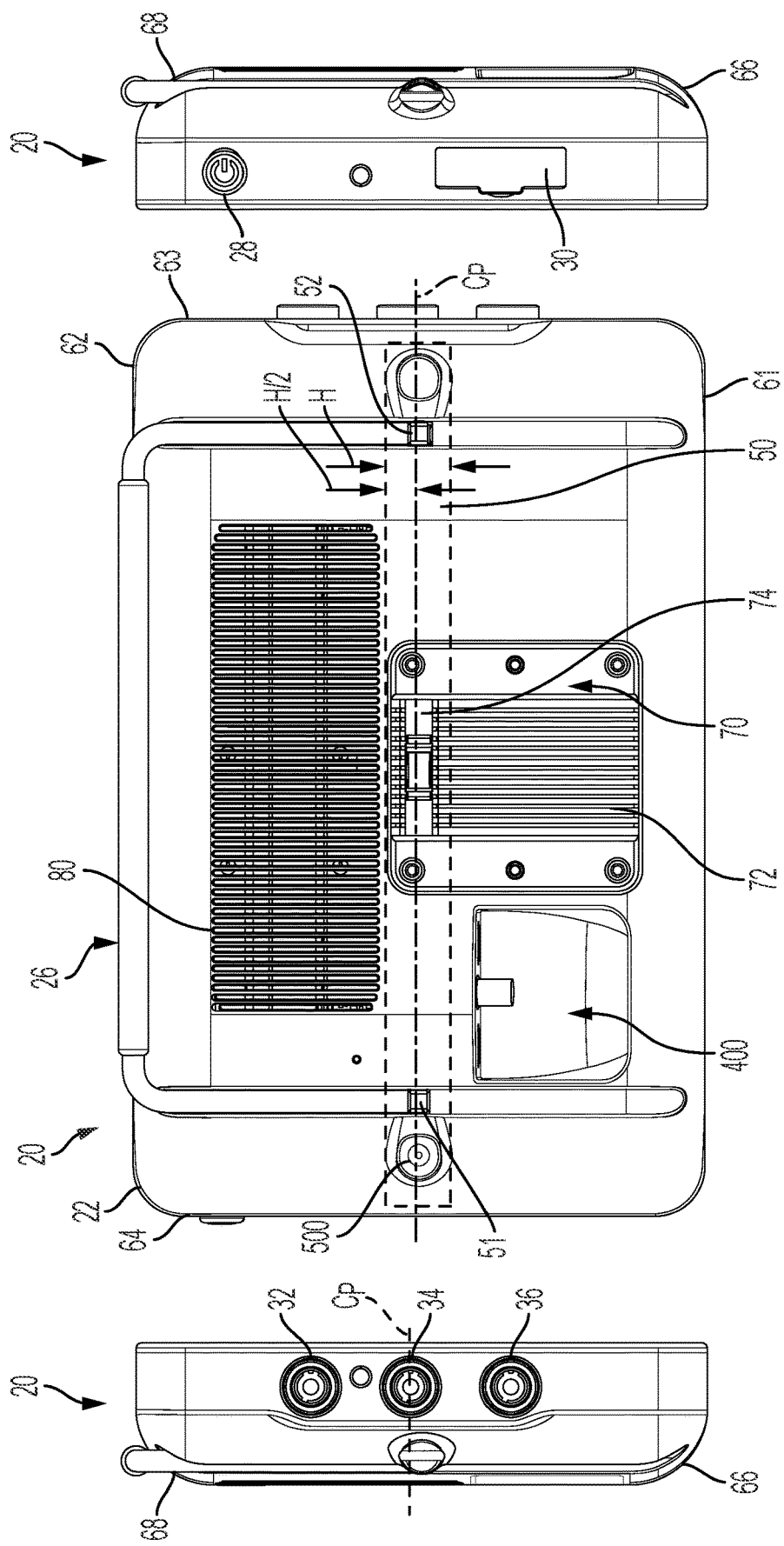

PORTABLE MEDICAL MONITOR

CROSS-REFERENCE TO RELATED APPLICATIONS

This application is a continuation of U.S. patent application Ser. No. 16/904,245, filed Jun. 17, 2020, now U.S. Pat. No. 10,835,106, issued Nov. 17, 2020, which claims the benefit of and priority from Danish Patent Application No. PA 2020 70116, filed Feb. 21, 2020, said applications are incorporated herein by reference in their entirety.

U.S. patent application Ser. No. 16/905,859, filed Jun. 18, 2020, issued as U.S. Pat. No. 10,980,397 on Apr. 20, 2021, claims priority from Danish Patent Application No. PA 2020 70117, filed Feb. 21, 2020, and claims related subject matter.

TECHNICAL FIELD

The disclosure relates to a portable monitor operable to present images obtained with a videoscope. More particularly, the disclosure relates to a monitor having a handle pivotally attached to a housing.

BACKGROUND OF THE DISCLOSURE

Medical videoscopes comprise endoscopes, colonoscopes, ear-nose-throat scopes, duodenoscopes, and any other medical device having an image sensor configured to obtain images of views of a patient. The term "patient" herein includes humans and animals. Portable medical monitors can be communicativelly coupled to the medical videoscopes to receive image data therefrom and present images corresponding to the image data on a display module of the monitor.

FIG. 1a is a perspective view of a videoscope 1 comprising a handle 2 with an articulation lever 4 and an insertion tube 3 having a proximal end 3a and a distal end 3b. An articulation tube 5 having an image sensor 6 is disposed at distal end 3b. The image sensor captures optical images and transmits image data corresponding to the images via a cable 12 to a connector 13. Connector 13 is insertable into a connector port of a monitor to present graphical images corresponding to the optical images with a display module of the monitor. Movement of articulation lever 4 reorients the field of view of image sensor 6.

Videoscopes are made for various procedures and may have different technical characteristics suited for the procedure they are designed to perform, based on the age of the device, or for other reasons. The technical characteristics, or technology, may comprise the type of image sensor included with the image sensor, whether the videoscope includes on-board data processing capabilities, whether the videoscope includes additional sensor which provide information to the monitor, potentially including more than one image sensor. The type of image sensor may provide different capabilities, including various controls such as image inversion, image rotation, contrast, and exposure.

An endoscope is a type of a videoscope. An endoscope described in commonly owned U.S. Patent Application No. 2019/0223694 has an insertion tube with an internal working channel and a connector at the handle adapted for the attachment of a syringe. A recess is adapted to accommodate a cylindrical body of the syringe when the syringe is attached to the connector. The endoscope is adapted to perform bronchoalveolar lavage, a procedure for obtaining samples, through the working channel, of organic material from a lung segment of a patient. Commonly owned U.S. Pat. No. 10,321,804 describes an articulated tip of an endoscope. Commonly owned U.S. Pat. No. 9,220,400 describes a camera housing arranged at the distal end of the insertion tube. The camera housing is molded and contains an image sensor and a light source, e.g. LED, embedded in the material of the camera housing. The foregoing application and patents describe technical characteristics of respective videoscopes described therein and are incorporated herein by reference in their entirety.

Furthermore, portable medical monitors are used in various settings including hospital, clinics, emergency response vehicles and in the field. These settings offer differing lighting conditions which might not be optimal for a predetermined monitor position.

Based on the foregoing it is evident that a need exists for a video processing apparatus suitable for use with a variety of videoscopes and videoscope technologies in a variety of settings.

SUMMARY OF THE DISCLOSURE

The present disclosure relates to a video processing apparatus, such as a portable medical monitor, and a method of using the video processing apparatus.

It is an object of the present disclosure to provide a solution which at least improves the solutions of the prior art. Particularly, it is an object of the present disclosure to provide a video processing apparatus that facilitates use in default and inverted orientations.

In a first aspect of the disclosure, a portable monitor operable in a first orientation and a second orientation is provided. In some embodiments according to the first aspect, the monitor comprises a display; a housing supporting the display, the housing having a first side and a second side opposite the first side, a third side and a fourth side opposite the third side and orthogonal to the first side, and a back side opposite the display, wherein in the first orientation the first side is below the second side and, and wherein in the second orientation the first side is above the second side; and a handle having arms and a bar extending between the arms, wherein the back side of the housing includes a middle section extending between the third side and the fourth side equidistantly between the first side and the second side, the middle section having a height less than 4.0 centimeters, and wherein each of the arms has a first end pivotally attached to the middle section of the housing and a second end opposite the first end and connected to the bar. In a variation of the present embodiment, the middle section has a height less than 3.0 centimeters.

In some embodiments according to the first aspect, a center plane bisects the housing in equal parts, and the handle axles comprise rotation axes lying in the center plane.

In some embodiments according to the first aspect, the housing comprises a rounded first edge connecting the first side to the back side and a rounded second edge connecting the second side to the back side, wherein the bar of the handle is operable to support the monitor at an angle to a horizontal plane ranging at least between 15-75 degrees, permitting the monitor to rest on the rounded first edge in the first orientation and on the rounded second edge in the second orientation.

In some embodiments according to the first aspect, wherein the back side of the housing includes grooves sized and shaped to receive, respectively, the arms of the handle.

In some embodiments according to the first aspect, the monitor comprises a handle axle connected to the first end of one of the arms, the handle axle traversing one of the grooves to define a first section of the groove on one side of the handle axle and a second section of the groove on an opposite side of the handle axle, wherein the handle is pivotable about the handle axle to a plurality of positions including a first position, in which the one of the arms is received by the first section of the groove, a second position, in which the one of the arms is received by the second section of the groove, and intermediate positions between the first position and the second position.

In a variation of the present embodiment, the monitor includes a handle position brake including one of the handle axles, a first disk having a surface including grooves defining protrusions therebetween, and a second disk having a surface including grooves defining protrusions therebetween, wherein the grooves of the first disk are shaped to match the protrusions of the second disk to thereby define the intermediate positions.

In another variation of the present embodiment, the monitor includes a handle position brake including the handle axle, a first disk, a second disk, and a spring, the handle axle passing through the first disk, the second disk, and the spring, and the spring causing a surface of the first disk to press against a surface of the second disk to create a braking force to maintain the handle in one of the plurality of positions.

In some embodiments according to the first aspect, the surface of at least one of the first disk and the second disk comprises grooves to increase the braking force relative to disk surfaces without grooves.

In a variation of the present embodiment, the grooves of the first disk extend radially and are evenly distributed. In one example, the grooves are evenly distributed at between 5 and 20 degrees from each other. Preferably the grooves are distributed at between 7 and 13 degrees, and more preferably at between 8 and 12 degrees, inclusive.

In some embodiments according to the first aspect, the housing comprises a rounded first edge connecting the first side to the back side and a rounded second edge connecting the second side to the back side, and the rounded first edge has a curvature radius equal to a curvature radius of the rounded second edge. In a variation of the present embodiment, the curvature radius of the rounded first edge is greater than 2.0 centimeters. Preferably the curvature radius is greater than 2.5 centimeters.

In some embodiments according to the first aspect, the monitor has a weight, wherein between 40-60% of the weight is between the handle axles and the first side of the monitor, and wherein between 40-60% of the weight is between the handle axles and the second side of the monitor.

In a second aspect of the disclosure, a portable monitor operable in a first orientation and a second orientation is provided. In some embodiments according to the second aspect, the monitor comprises a display; a housing supporting the display, the housing having a first side and a second side opposite the first side, a third side and a fourth side opposite the third side and orthogonal to the first side, and a back side opposite the display, wherein in the first orientation the first side is below the second side and, and wherein in the second orientation the first side is above the second side; a handle having arms, the arms having first ends opposite second ends, and a bar extending between and connected to the second ends of arms; and handle axles connected to the first ends of the arms to pivotally connect the handle to the housing, wherein the back side of the housing includes grooves sized and shaped to receive, respectively, the arms of the handle, and wherein the handle axles traverse, at least partially, the grooves to define first sections of the grooves on one side of the handle axles and second sections of the grooves on opposite sides of the handle axles, wherein the handle is pivotable about the handle axles to a plurality of positions including a first position, in which the arms are received by the first sections of the grooves, a second position, in which the arms are received by the second sections of the grooves, and intermediate positions between the first position and the second position.

In some embodiments according to the second aspect, the monitor includes a handle position brake including one of the handle axles, a first disk having a surface including grooves defining protrusions therebetween, and a second disk having a surface including grooves defining protrusions therebetween, wherein the grooves of the first disk are shaped to match the protrusions of the second disk to thereby define the intermediate positions.

In some embodiments according to the second aspect, the grooves of the first disk are evenly distributed at between 5 and 20 degrees. Preferably the grooves are distributed at between 7 and 13 degrees, and more preferably at between 8 and 12 degrees, inclusive In some embodiments according to the second aspect, the housing comprises a rounded first edge connecting the first side to the back side and a rounded second edge connecting the second side to the back side, and the rounded first edge has a curvature radius equal to a curvature radius of the rounded second edge.

In some embodiments according to the second aspect, the monitor has a weight, wherein between 40-60% of the weight is between the handle axles and the first side of the monitor, and wherein between 40-60% of the weight is between the handle axles and the second side of the monitor.

In a third aspect of the disclosure, a method of using a monitor according to any of the embodiments of the first or second aspects is provided. In some embodiments according to the third aspect, the method the comprises placing the monitor in the first orientation on a support structure with the handle in a first of the plurality of intermediate positions; pivoting the handle to a second of the plurality of positions; and prior to or after pivoting the handle to the second of the plurality of positions, placing the monitor in the second orientation on the support structure.

BRIEF DESCRIPTION OF THE DRAWINGS

The above-mentioned embodiments and additional variations, features and advantages thereof will be further elucidated by the following illustrative and nonlimiting detailed description of embodiments disclosed herein with reference to the appended drawings, wherein:

FIGS. 4a, 4b, and 4c are side and back views of the embodiment of the portable medical monitor of FIG. 1b;

FIG. 9a is a top view of the embodiment of the support bracket of FIG. 6a;

FIG. 10 is a perspective view of an embodiment of a component of the support bracket of FIG. 8a;

FIGS. 14a and 14b are partial views of components of the portable medical monitor of FIG. 1a;

In the drawings, corresponding reference characters indicate corresponding parts, functions, and features throughout the several views. The drawings are not necessarily to scale and certain features may be exaggerated in order to better illustrate and explain the disclosed embodiments.

DETAILED DESCRIPTION

Figure 1A:
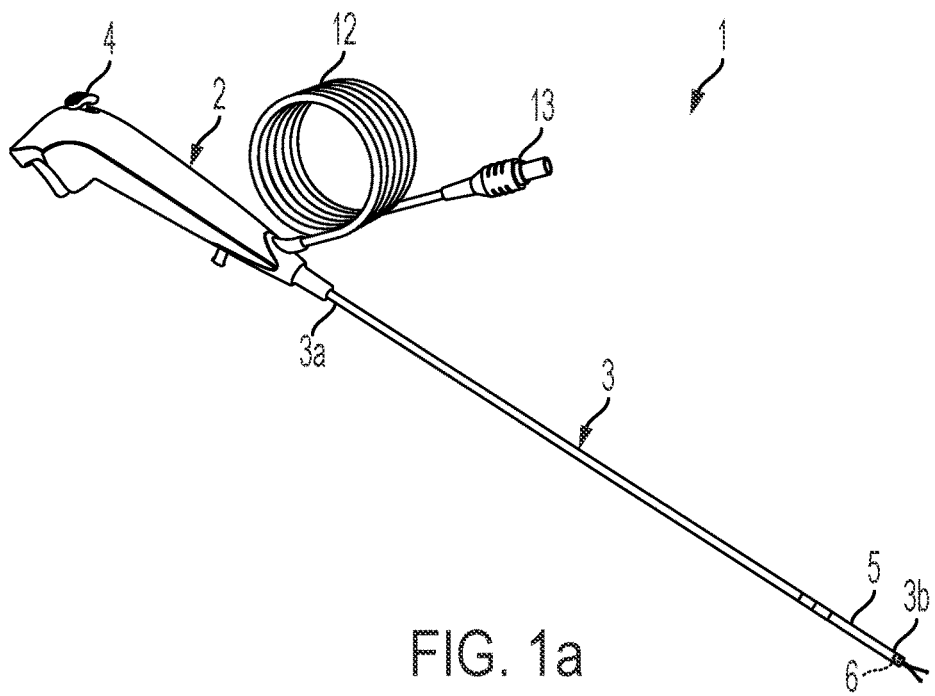
FIG. 1a is a perspective view of an embodiment of a videoscope.

For the purposes of promoting an understanding of the principles of the disclosure, reference will now be made to the embodiments illustrated in the drawings, which are described below. The embodiments disclosed below are not intended to be exhaustive or limit the disclosure to the precise form disclosed in the following detailed description.

Figure 1B:
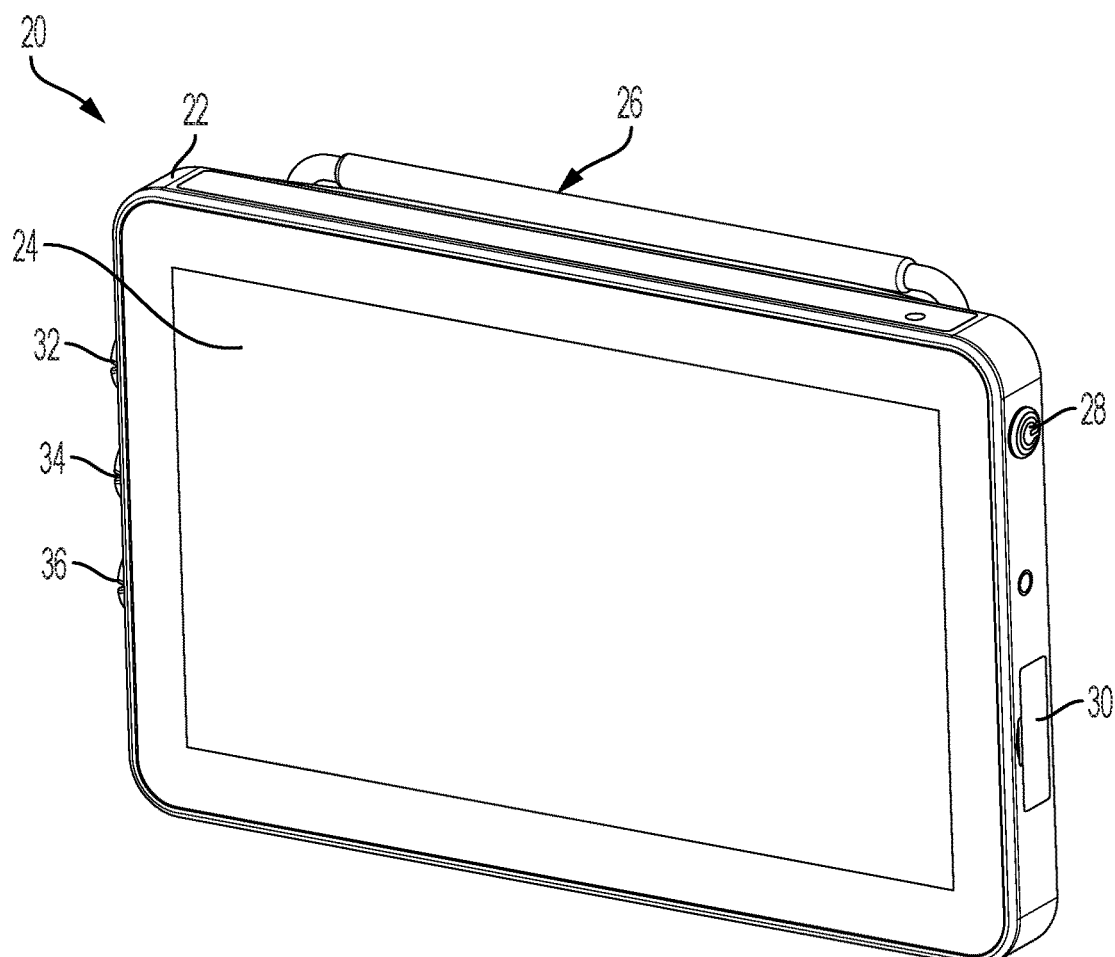
FIG. 1b is a perspective view of an embodiment of a portable medical monitor.
Figure 2A:
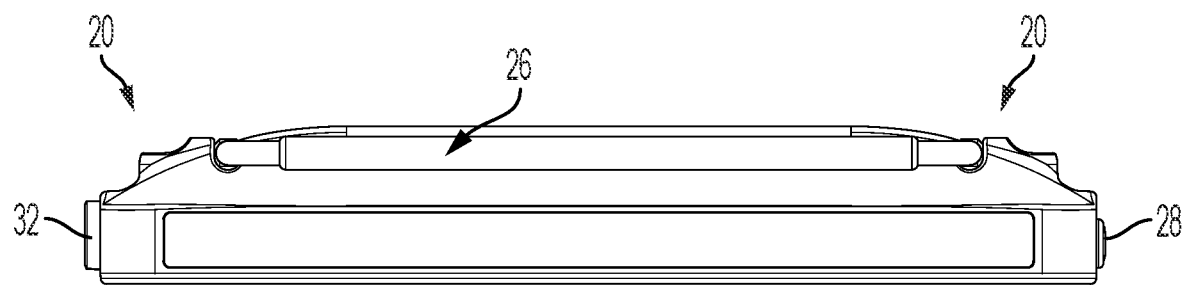
FIGS. 2a-c are top, front, and bottom views of the embodiment of the portable medical monitor of FIG. 1b in a first orientation.
Figure 2B:
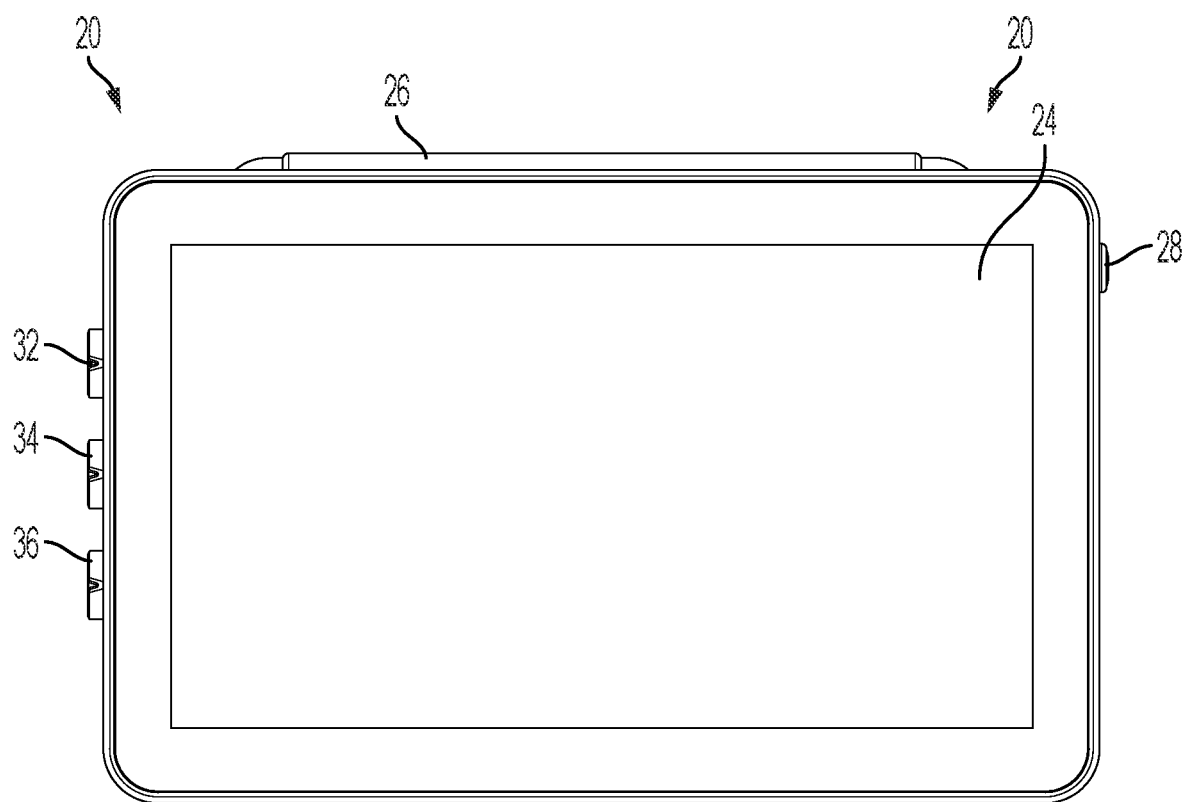
Figure 2C:
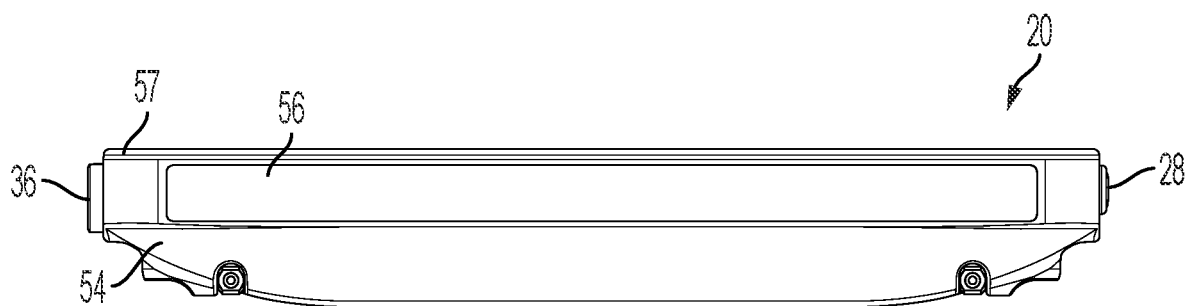

FIG. 1b is a perspective view of an embodiment of a portable medical monitor 20 (also referred to as "monitor 20") in a first orientation. FIGS. 2a-c are top, front, and bottom views of monitor 20. As shown, monitor 20 comprises a housing 22, a display module 24 supported by housing 22, a handle 26, a power button 28, an output interface 30, and connector ports 32, 34, and 36. Monitor 20 has front and back sides. Display module 24 includes a display screen that defines the front side and electronic circuits operable to receive, and then output to the display screen, video data. The display screen may be a touch sensitive screen that also functions as a user input sensor, in which case the electronic circuits also include circuits to sense the position of the user's fingers or input device, e.g. touch screen pencil, and to output signals including indicia indicative of the location touched on the display screen.

As shown in FIG. 2c, housing 22 includes a front housing component 57 removably attached to a back housing component 54. A securement cover 56 is removably attached to back housing component 54. Securement cover 56 can be removed to expose and provide access to a number of fasteners provided to removably attach front housing component 57 to back housing component 54. Example fasteners include screws and snap-fits.

Figure 3A:
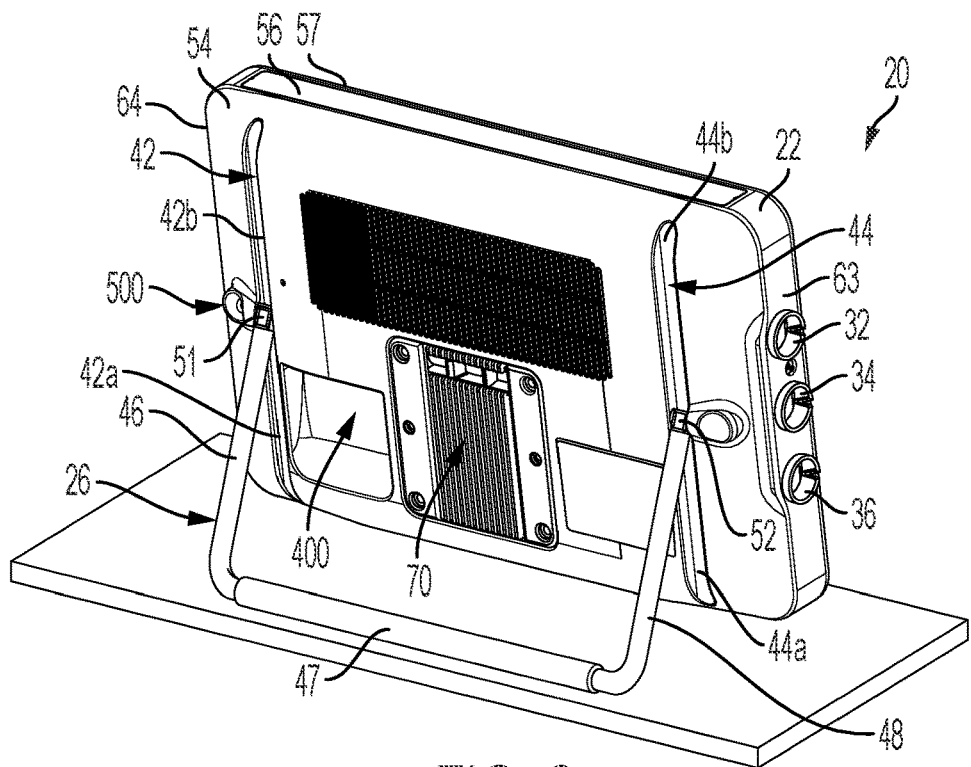
FIGS. 3a and 3b are perspective and side views of the embodiment of the portable medical monitor of FIG. 1b.
Figure 3B:
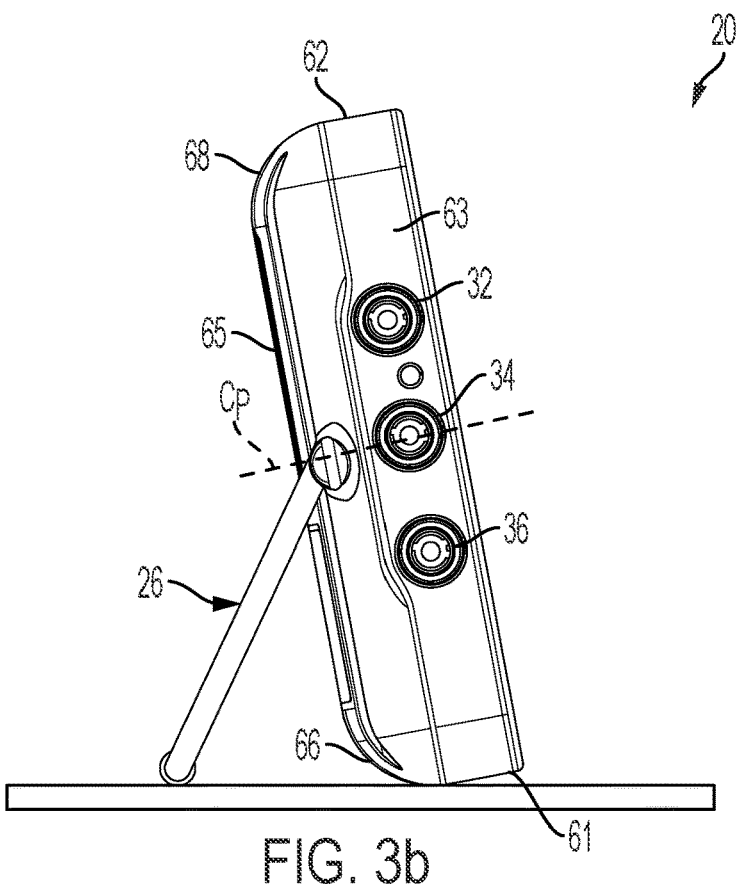
Figure 5A:
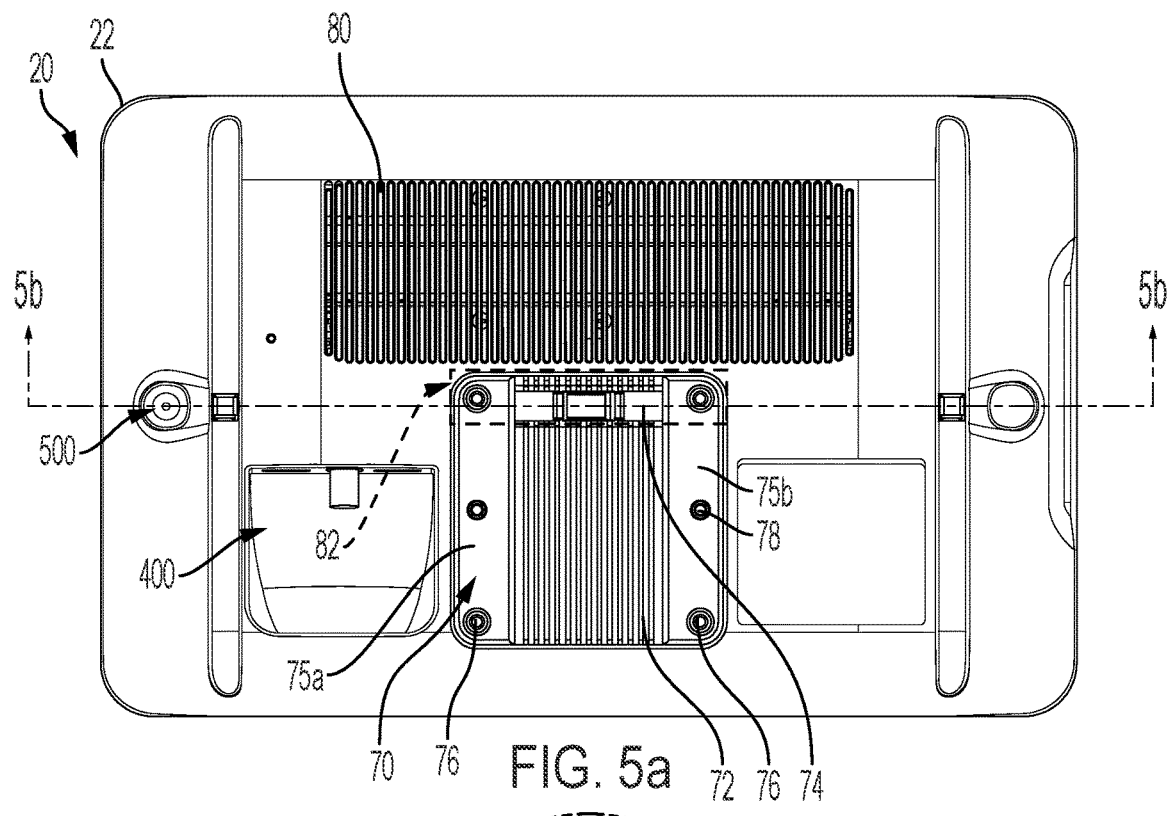
FIGS. 5a, 5b, and 5c are back, cross-section, and expanded cross-section views of the embodiment of the portable medical monitor of FIG. 1b.

FIGS. 3a and 3b are a back perspective and a side view of monitor 20. Monitor 20 comprises support features including at least handle 26 and a latching structure 82, described with reference to FIGS. 5a-5c, including a pair of bracket latch receivers. Handle 26, described with reference to FIGS. 3a-4c, can be used to carry monitor 20 and can function as a table stand. Latching structure 82 is configured to support monitor 20 from a monitor bracket which can be clamped to an IV stand. Advantageously, the support features are positioned in a middle section of the monitor to facilitate operation of the monitor in the first and second orientations. Rotating the monitor to place the connector ports on the right or left side may be desirable in enclosed settings, for example, which may provide limited accessibility to one or the other side. Advantageously, connector rings are provided on one side of the monitor that distinguish the right and left sides and allow a user to quickly determine which orientation the monitor is in.

Handle 26 comprises handle axles 51, 52 pivotally securing arms 46, 48 to housing 22. Each handle axle is connected to the first end of one of the arms. Each handle axle traverses, at least partially, one of the grooves 42, 44 to define a first section of the groove on one side of the handle axle and a second section of the groove on an opposite side of the handle axle. The handle is pivotable about the handle axles to a plurality of positions including a first position, in which the arms are received by the first sections of the grooves, a second position, in which the arms are received by the second sections of the grooves, and intermediate positions between the first position and the second position. Monitor 20 further includes handle position brakes (described with reference to FIGS. 18 and 19), including the handle axles, to hold the handle in one of the positions. Housing 22 includes a body 54 and a cover 56. Cover 56 can be removed from body 54 to provide access to fasteners which can be removed to separate body 54 from display module 24 and provide access to various internal components.

The back side, 65, of the housing includes grooves 42, 44 sized and shaped to receive, respectively, arms 46, 48 of handle 26. The back side of the housing also includes a middle section 50 (shown in FIG. 4b) extending between the third side and the fourth side equidistantly between the first side and the second side, the middle section having a height "H" less than 4.0 centimeters, preferably less than 3.0 centimeters. A central plane $C_P$ passes through middle section 50. Each of the arms has a first end pivotally attached via a handle axle 51, 52 to the middle section of the housing, as described further below, and a second end opposite the first end and connected to the bar. Handle axles 51, 52 are shown on central plane $C_P$. Grooves 42, 44 each have a portion 42*a*, 44*a* on one side of a handle axle and another portion 42*b*, 44*b* on the other side of the handle axle. The portions of grooves 42, 44 are sized and shaped to receive the arms of the handle. In FIGS. 3*a* and 3*b* the arms of the handle are not drawn to scale.

Figure 20C:
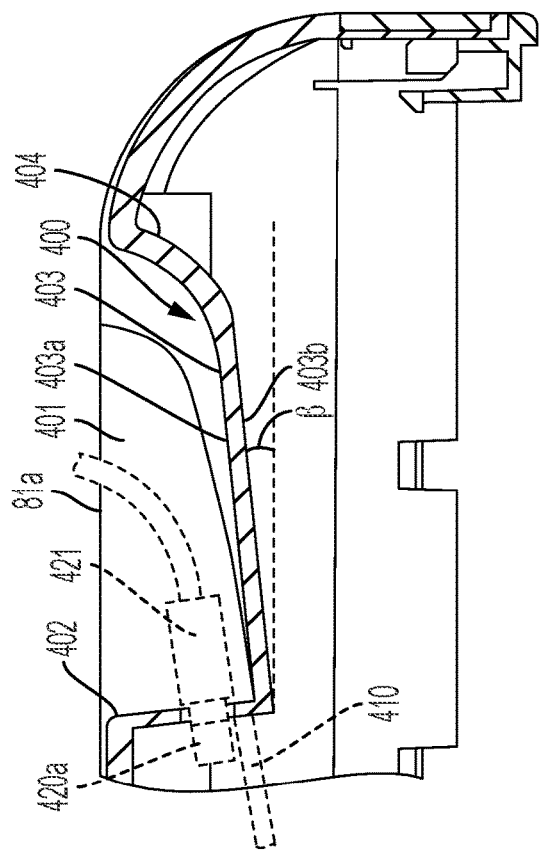
FIGS. 20a, 20b, and 20c are perspective views of an embodiment of a video output housing recess.
Figure 20A:
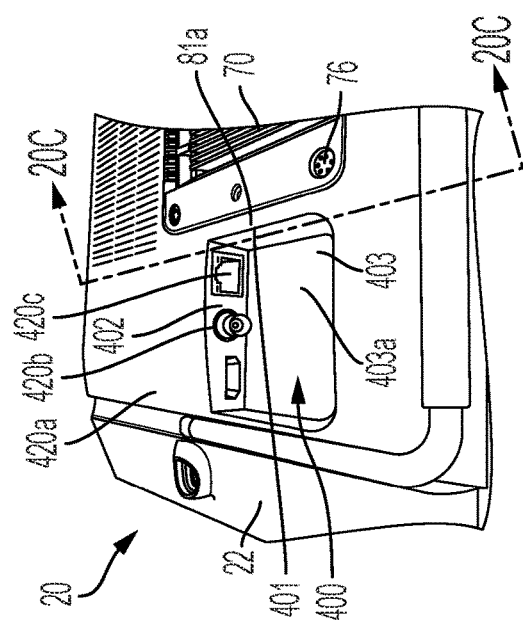
Figure 20B:
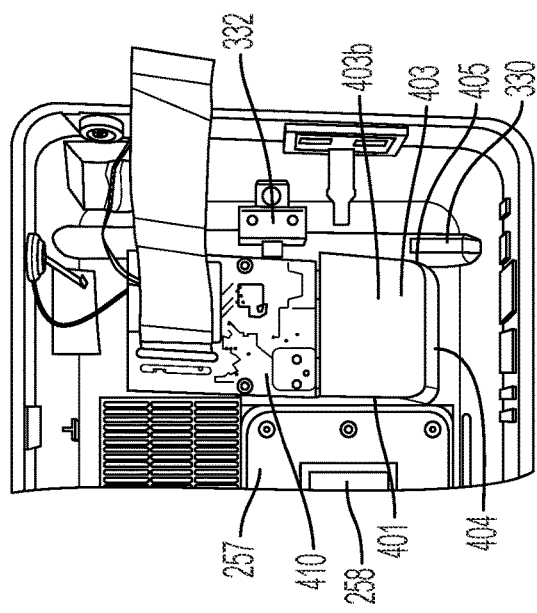
Figure 21:
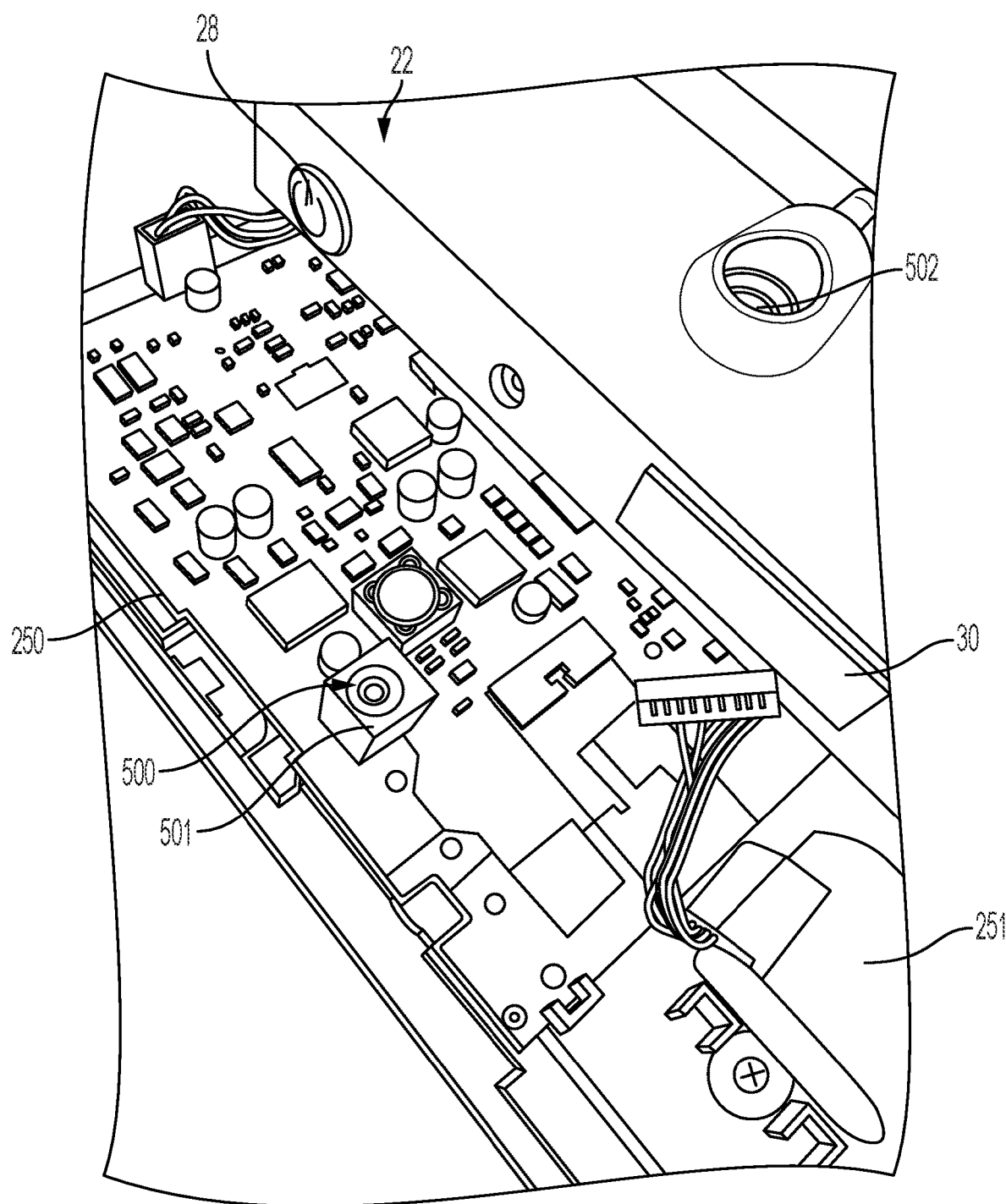
FIG. 21 is a perspective view of the portable medical monitor of FIG. 1b in a partially disassembled state.

Housing 22 also includes a video output housing recess 400 (described with reference to FIGS. 20*a-c*) and a power receptacle assembly 500 (described with reference to FIGS. 14*a* and 21). Additionally, housing 22 includes an external heat sink 70.

Housing 22 has a first side 61 and a second side 62 opposite the first side, a third side 63 and a fourth side 64 opposite the third side and orthogonal to the first side, a front side, and a back side opposite the front side. Advantageously, monitor 20 can be rotated 180 degrees from a first orientation to a second orientation. The first orientation may be referred to as the "default" orientation and the second orientation may be referred to as the "inverted" orientation. In the default, or first, orientation the external heat sink is below a ventilation grid and first side 61 is below second side 62. In the inverted, or second, orientation first side 61 is above the second side 62. The connector ports are on the third side. In the first orientation the third side is the left side and in the second orientation the third side is the right side. The terms "right" and "left" correspond to the sides of a viewer facing display module 24. Accordingly, in FIGS. 3*a* and 3*b* the top side is the side opposite the support structure onto which monitor 20 rests because monitor 20 is in the first orientation with connector ports 32, 34, and 36 on the left side.

Portable medical monitor 20 includes sensors configured to determine a change in the orientation of monitor 20 (e.g. between the first and second orientations) and a controller configured to rotate the images presented with display module 24 responsive to such rotation. The sensors and controller are described with reference to FIGS. 22 and 23.

Referring to FIG. 3*b*, monitor 20 has rounded edges. A rounded first edge 66 connects first side 61 to back side 65 and a rounded second edge 68 connects second side 62 to back side 65. The bar of the handle is operable to support the monitor at an angle to a horizontal plane, as shown in FIG. 3*b*, ranging at least between 15-75 degrees, permitting the monitor to rest on the rounded first edge in the first orientation and on the rounded second edge in the second orientation. Handle brakes, described with reference to FIGS. 18 and 19, maintain a position of the handle to support monitor 20 at a plurality of angles relative to the support structure onto which monitor 20 lays.

In some embodiments, rounded first edge 66 has a curvature radius equal to a curvature radius of rounded second edge 68. The curvature radius may be greater than 2.0 centimeters, and preferably greater than 2.5 centimeters.

FIGS. 4*a*, 4*b*, 4*c*, 5*a*, 5*b*, and 5*c* depict support features of monitor 20 including latching structure 82, including bracket latch receivers operable to receive latches of a monitor support bracket described with reference to FIGS. 8*a*-9*b*. FIG. 4*b* illustrates the back side of monitor 20 showing the arms of handle 26 in the grooves. A ventilation grid 80 is positioned between the grooves and also between second side 62 and central plane $C_P$.

Referring to FIG. 4*b*, a heat sink 70 extends downward from middle section 50 toward first side 61. Heat sink 70 includes a plurality of fins 72 with slots therebetween configured to extend the external surface area of heat sink 70 and thereby increase cooling capacity, as is know in the art. An aperture 74 of heat sink 70 is positioned on the middle section of the monitor. Central plane $C_P$ is equidistant between first side 61 and second side 62 and divides middle section 50 such that a first side of the middle section has a height equal to H/2 and a second side of the middle section has a height equal to H/2. As shown, an edge of heat sink 70 is aligned with an edge of middle section 50. Generally, the latching structure comprises latch retainers 85*a*, 85*b* and recesses 86*a*, 86*b*. In one variation, the latching structure is part of heat sink 70 and is therefore secured to housing 22 when heat sink 70 is secured to housing 22. In another variation, a portion of latching structure 82, e.g. a centering portion, is formed with the back wall of housing 22. Aperture 74 surrounds the portion of the latching structure 82 formed with the back wall of housing 22. In a further embodiment, the portion of the latching structure 82 is formed in a separate device that fits between the back wall of housing 22 and heat sink 70, as described with reference to FIG. 6.

Figure 5B:
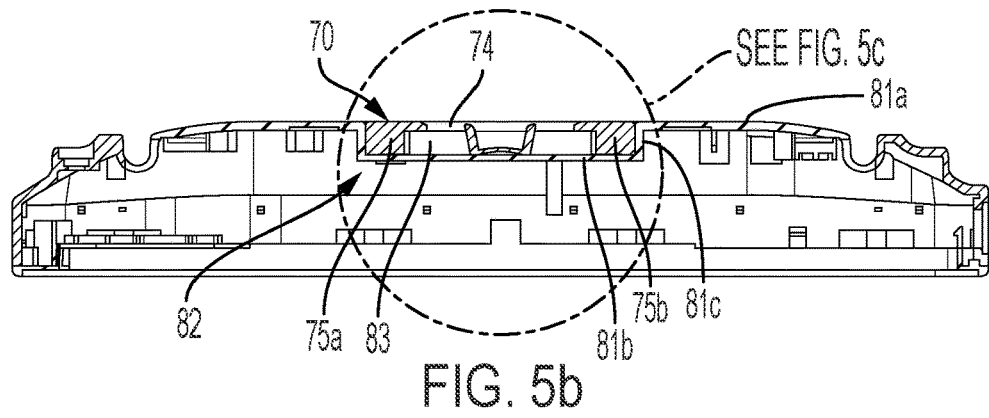
Figure 5C:
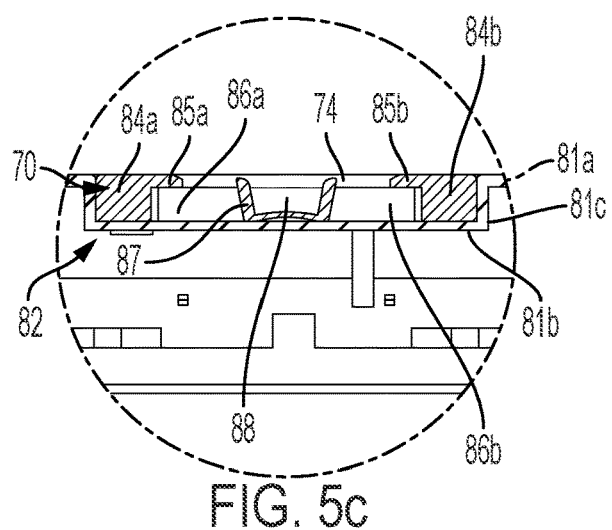

FIG. 5*b* is a cross-sectional view of monitor 20 at central plane $C_P$ showing latching structure 82. The handle axles comprise rotation axes lying in the center plane. FIG. 5*c* is an expanded view of the cross-sectional view of latching structure 82. As shown, heat sink 70 is positioned within a recess 83 formed in the back side of the monitor by lateral walls 81*c* extending from a wall 81*a* (which forms back side 65 of housing 22) and a recessed heat sink wall 81*b* connecting lateral walls 81*c*. Heat sink recess 83 is sized to receive heat sink 70 therein. Heat sink 70 includes two vertical, parallel, support walls 75*a*, 75*b*. Support walls 75*a*, 75*b* include a securement portion 84*a*, 84*b*, and extending from the securement portions toward the center of the heat sink, a first latch retainer 85*a* and a second latch retainer 85*b*. A plurality of screws 76 pass through the securement portions to secure heat sink 70 to housing 22. Between first and second latch retainers 85*a*, 85*b* and recessed heat sink wall 81*b* of housing 22, are a first recess 86*a* and a second recess 86*b*. The latch retainers 85*a*, 85*b* cause latches of the support bracket to retreat until the latches enter the recesses, at which time the latches are retained by the latch retainers. As shown, latching structure 82 includes a centering structure 87 comprising two vertical walls defining a cavity 88. Cavity 88 is sized to receive a centering protrusion 168 (shown in FIGS. 8*a* and 8*b*) from the monitor support bracket, which facilitates latching of the monitor onto the monitor support bracket.

Figure 6:
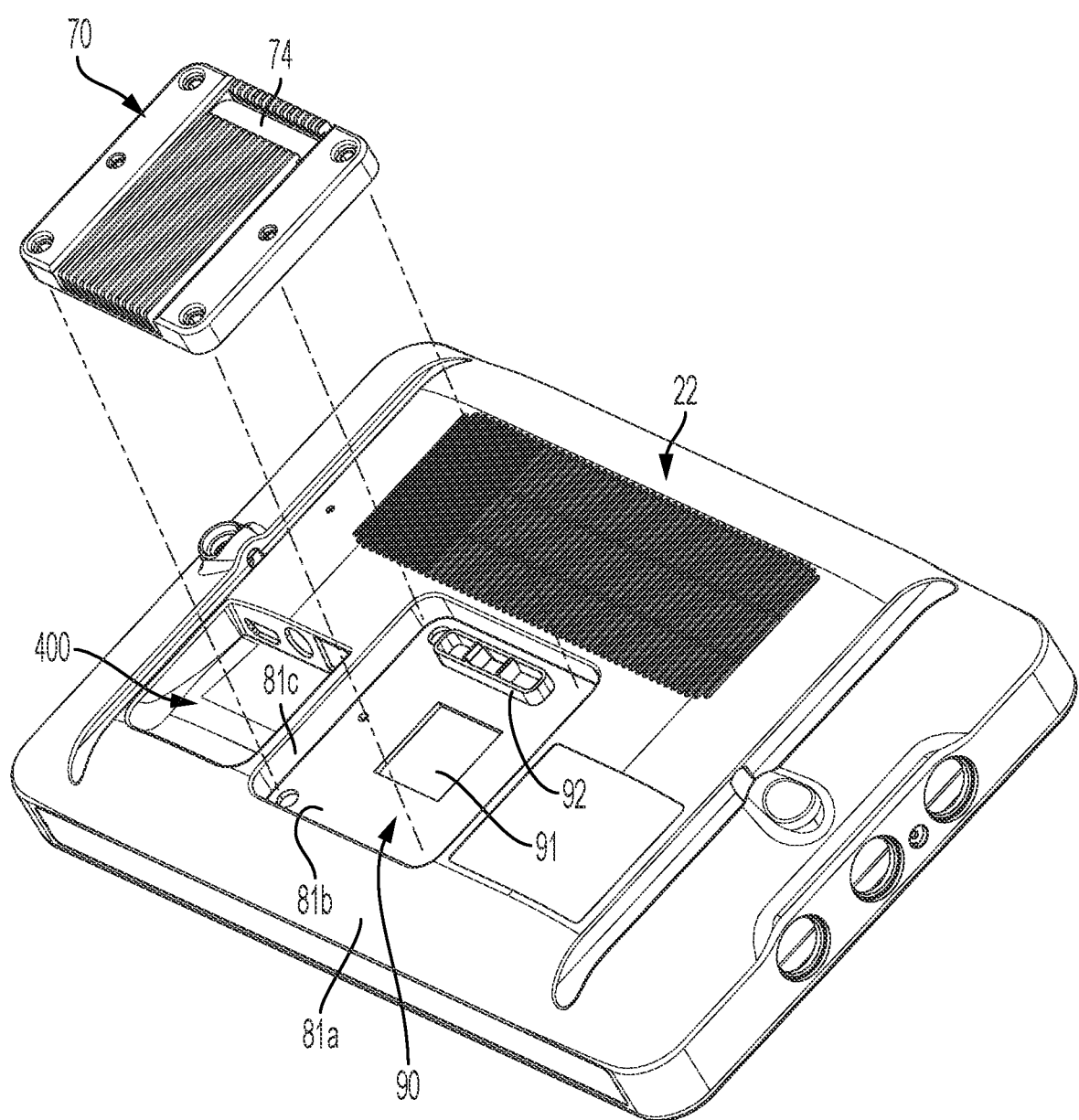
FIG. 6 is a perspective exploded view of the portable medical monitor of FIG. 1b.
Figure 7:
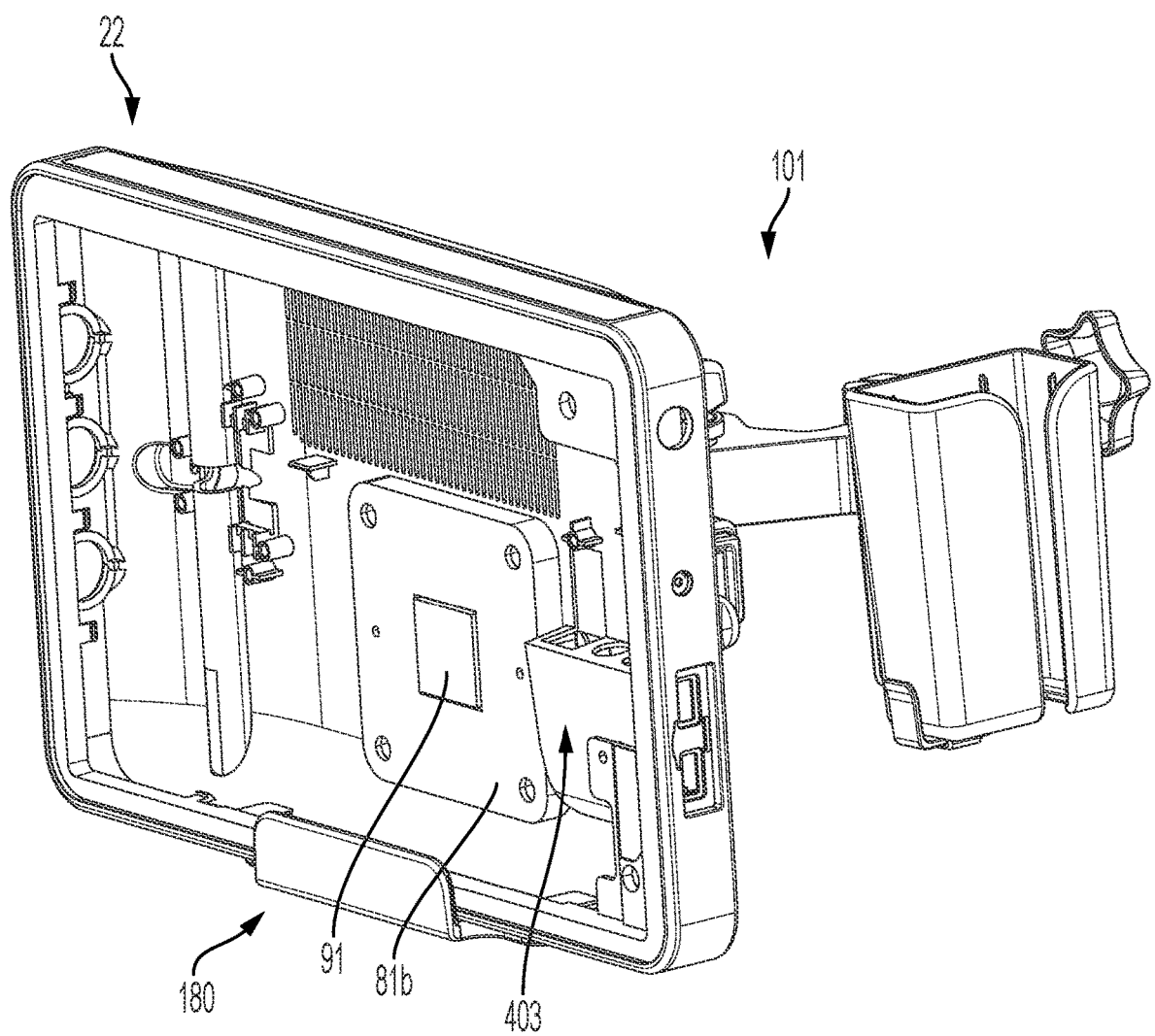
FIG. 7 is a perspective view of an embodiment of a housing of the portable medical monitor of FIG. 1b supported by a support bracket.
Figure 8A:
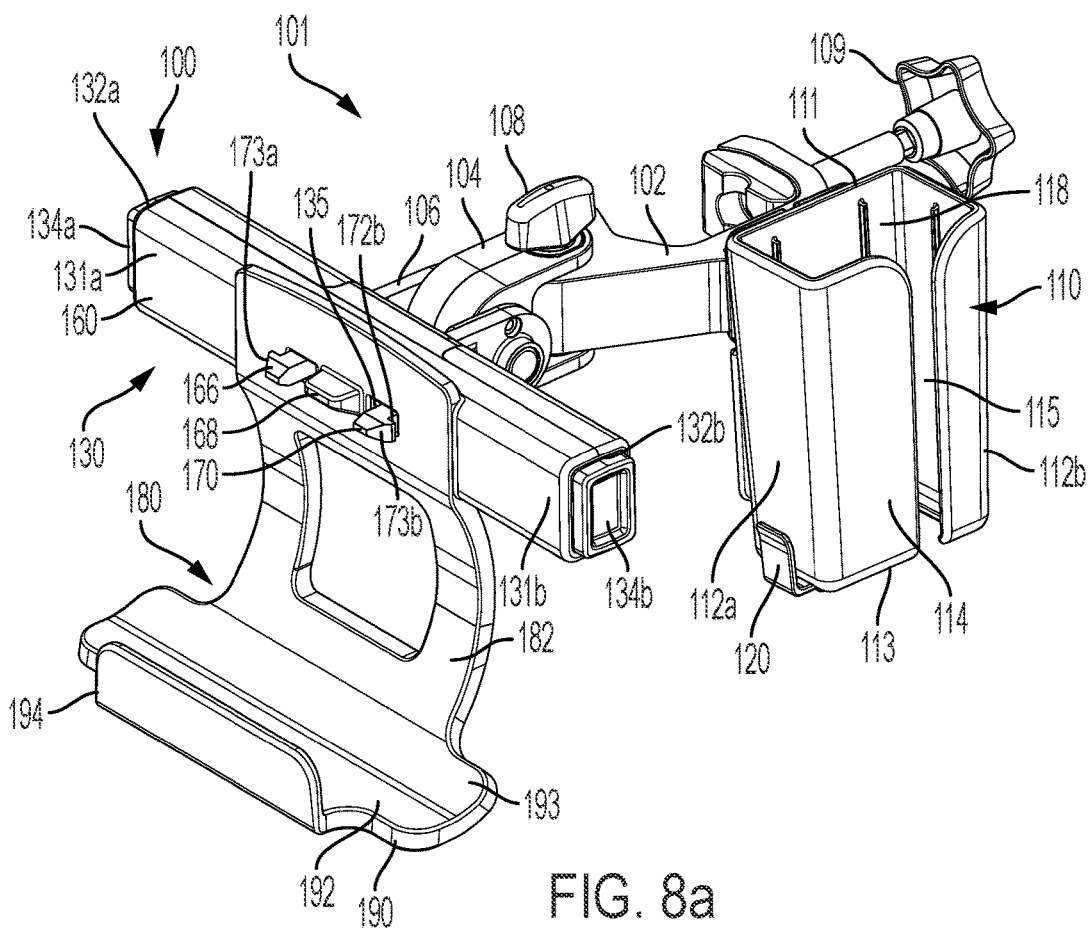
FIGS. 8a and 8b are perspective and side views of an embodiment of a support bracket for the portable medical monitor of FIG. 1b.
Figure 8B:
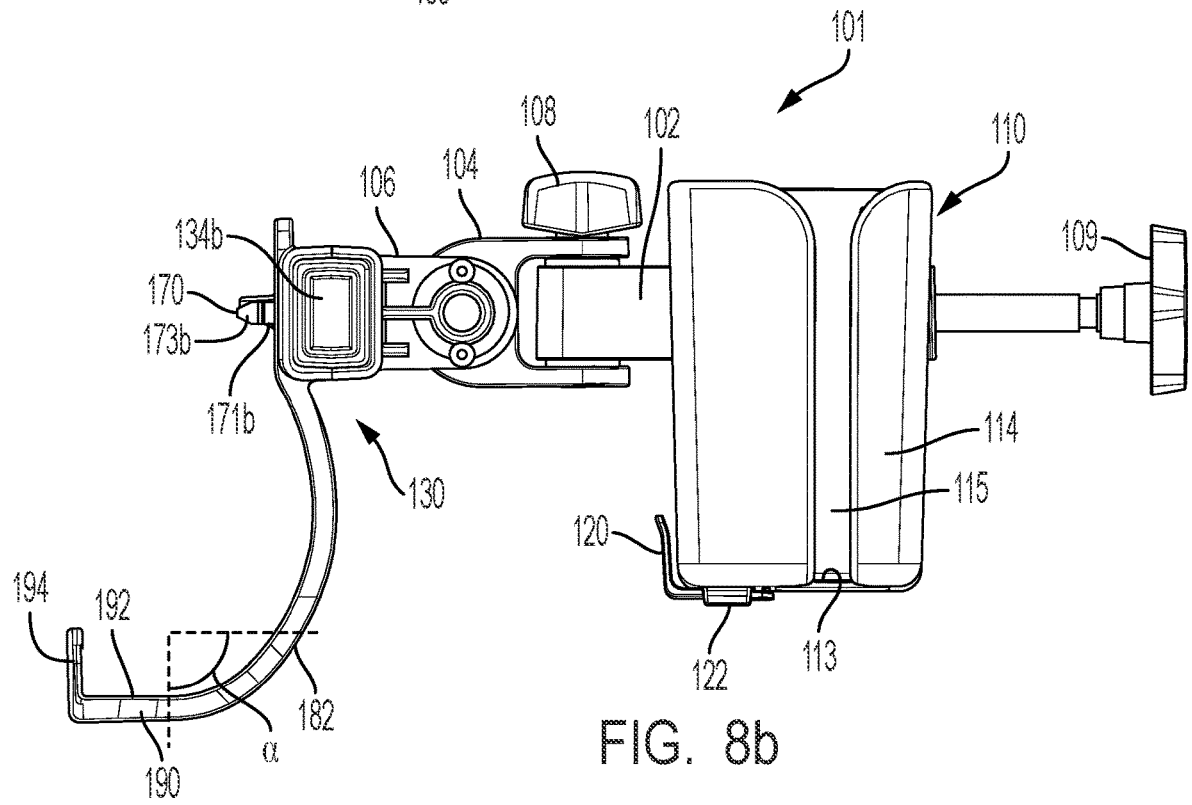

FIG. 6 is a perspective exploded back view of monitor 20 illustrating a variation of the latching structure described above and FIG. 7 is a perspective view of housing 22 supported by a monitor support bracket 100, depicted in FIGS. 8*a* and 8*b*. Referring to FIG. 6, housing 22 includes video output housing recess 400 and a heat sink recess 90 defined by a plurality of walls including lateral walls 81*c* extending from a back wall 81*a* of housing 22 toward the internal space of monitor 20, and a recessed heat sink wall 81*b* connecting lateral walls 81*c*. Recessed heat sink wall 81*b* includes a through-hole 91 through which heat sink 70 is thermally connected to a heat generator located in the internal space. A latching structure centering portion 92 is shown extending from recessed heat sink wall 81*b*. A heat generator can be any packaged integrated circuit that generates heat. In particular, a heat generator may be a packaged integrated circuit which may suffer a reduced life or performance unless heat is removed from it. Examples of heat generators include processors including central processing units, graphical processing units, FPGAs, other packaged circuits capable of executing processing instructions, and the like.

The handle axles comprise rotation axes lying in the center plane. In use, latches 166, 170 from the monitor support bracket (shown in FIGS. 8a and 8b) pass through aperture 74. The latches are movable between a first position and a second position and are biased to the first position. The latches include angled surfaces that contact first and second latch retainers 85a, 85b. During insertion the monitor is pressed toward the monitor support bracket and the latches pass through the aperture. The first latch retainer and the second latch retainer cause the two latches to temporarily move to the second position and after insertion the latches return to the first position with portions of the latches positioned in the bracket latch receivers intermediate the first latch retainer and the display module and intermediate the second latch retainer an the display module to secure the monitor to the monitor support bracket. The latches move away from each other and into first and second recesses 86a, 86b by operation of a biasing force.

Advantageously, heat sink 70 is manufactured from a material that is stronger than the material from which housing 22 is made, therefore heat sink 70 supports or provides support for hanging monitor 20 from the monitor support bracket. For example, heat sink 70 can be made from aluminum or other heat conductive metals, and housing 22 can be made from polymers. Additionally, placing latching structure 82 in the middle section of the monitor allows hanging the monitor in the first orientation or the second orientation with the first or second sides supported by the cradle of the support frame.

Figure 9A:
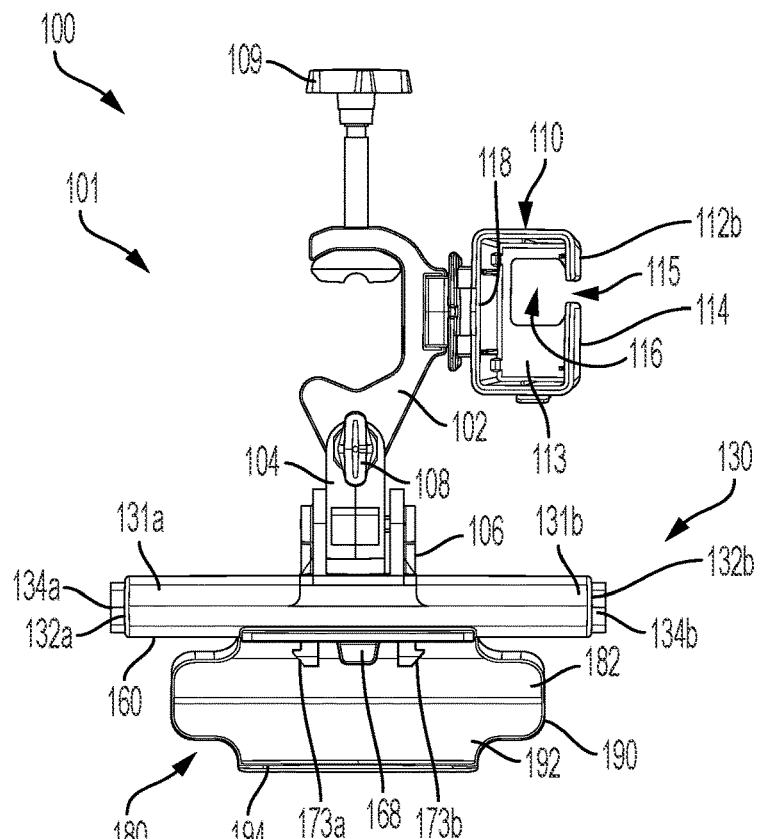
Figure 9B:
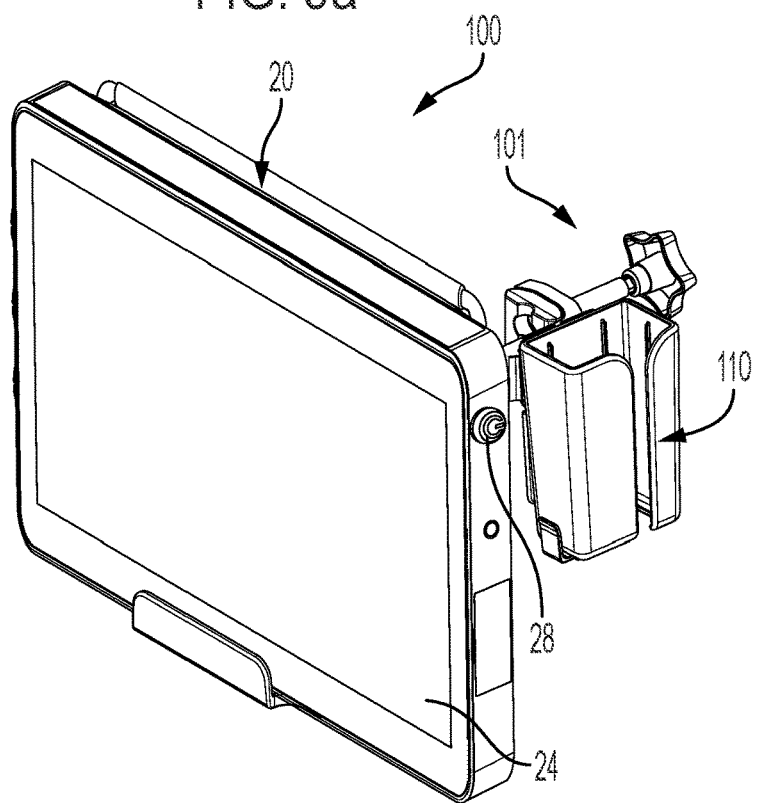
FIG. 9b is a perspective view of the embodiment of the support bracket of FIG. 6a supporting the portable medical monitor of FIG. 1b.
Figure 10:
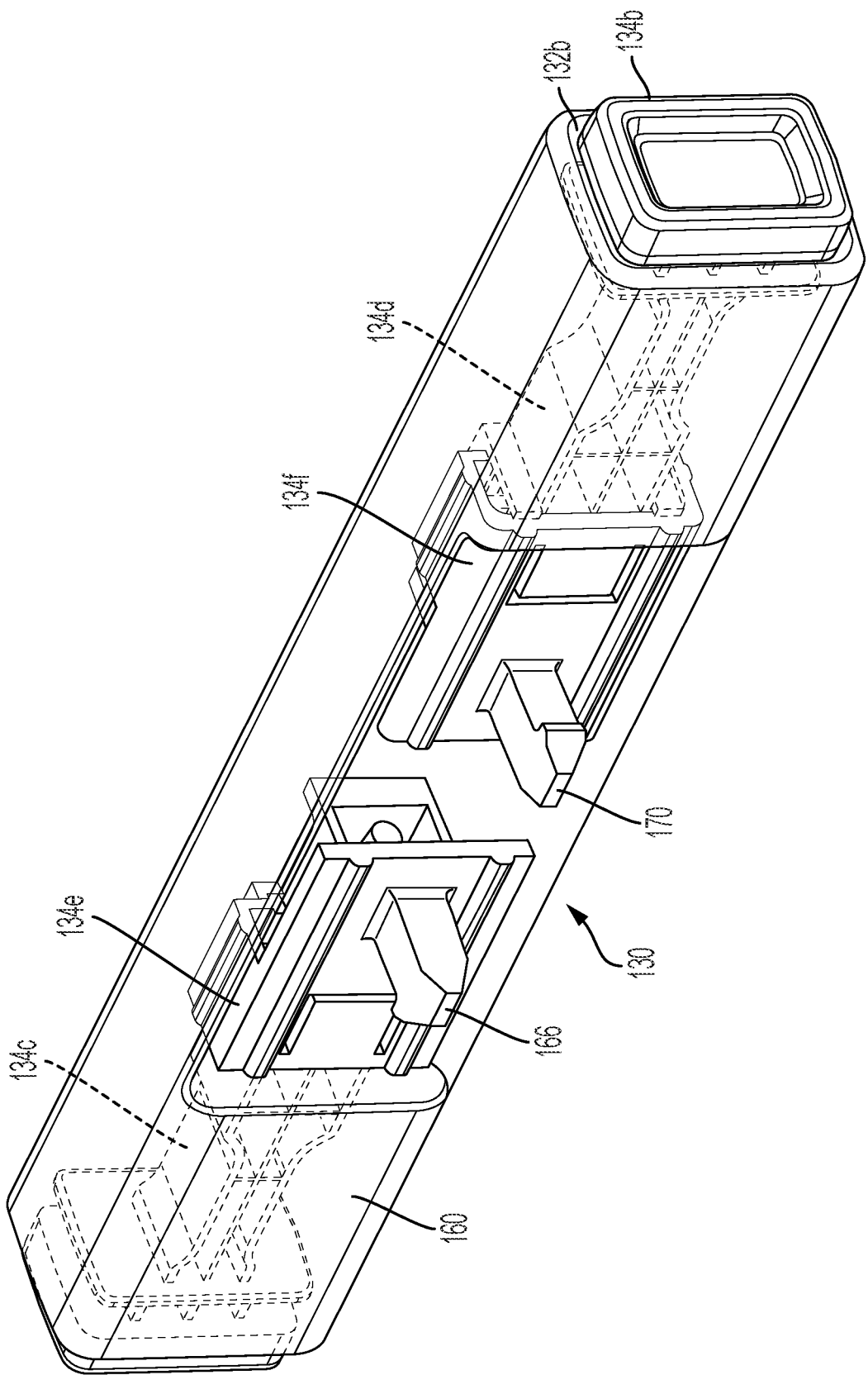
Figure 11:
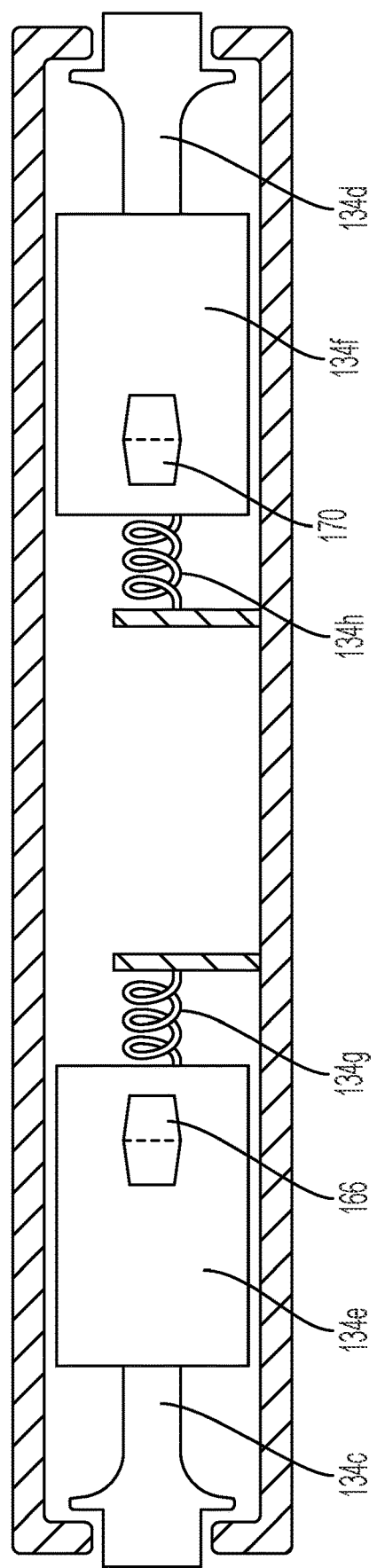
FIG. 11 is schematic view of a cross-section of the component of the support bracket of FIG. 10.

FIGS. 8a, 8b, 9a, 9b, 10, and 11 are views of an embodiment of a support bracket 100 for monitor 20 including an articulating arm 101 and a longitudinal frame 130. FIG. 9b shows monitor 20 mounted on support bracket 100. FIGS. 10 and 11 show details of longitudinal frame 130. Articulating arm 101 includes a clamp 102 hinged to a horizontally articulating link 104 which is hinged to a vertically articulating link 106. A knob 108 can be rotated to tighten a hinge between horizontally articulating link 104 and vertically articulating link 106 in a known manner. Clamp 102 also includes a threaded rod connected to a knob 109 which can be rotated to tightly secure clamp 102 to a support rod passing through an aperture of the clamp, in a known manner. The support rod can be an IV stand, for example.

A cable holster 110 is removably attached to clamp 102 and comprises a support wall 111 attached to the clamp, side walls 112a, 112b extending from the support wall, a bottom wall 113, and an exterior wall 114 opposite the support wall and connected to the lateral walls and the bottom wall, the support wall, the side walls, the bottom wall, and the exterior wall defining a volume 118 in which a power cable of the monitor may be held. Exterior wall 114 has a slot 115 along a length thereof sized and configured to pass therethrough a portion of the power cable. A cable clip 120 and clip retainer 122 are also shown.

Longitudinal frame 130 includes a first end 131a having a first opening 132a, a second end 131b having a second opening 132b, a monitor facing side 160 between the first opening and the second opening, and at least one aperture 135 disposed in the monitor facing side. A first actuator 134a at the first end of the longitudinal frame translates through the first opening and a second actuator 134b at the second end of the longitudinal frame translates through the second opening. Referring to FIG. 10, first and second actuators 134a, 134b include internal portions 134c, 134d which extend to contact a pair of longitudinally aligned latches 166, 170 movable between a first position and a second position and biased to the first position. The biasing force may be provided by springs 134g (shown in FIG. 11), for example, connecting internal portions 134e, 134f of the latches to the walls of the elongate member and compressible by operation of first and second actuators 134a, 134b to overcome the biasing force. A gap between the pair of latches is greater in the first position than the second position. Each of the pair of latches includes an internal portion 134e, 134f disposed within the longitudinal frame, a protruding portion 171b (shown in FIG. 8b) connected to the internal portion and extending through the at least one aperture, and a latching portion 172b connected to the protruding portion distally of the monitor facing side and including an angled surface 173a, 173b. The angled surfaces of the pair of latches are operable to move the pair of latches from the first position to the second position. The first actuator and the second actuator are also operable to move the pair of latches from the first position to the second position. The biasing member, for example a spring, moves the pair of latches from the second position to the first position.

In one variation, internal portions 134e, 134f of the latches are attached to internal portions 134c, 134d of the actuators. In another variation, internal portions 134c, 134d press against but are not attached to internal portions 134e, 134f. Internal portions 134e 134f may be inserted through the opening on the monitor facing side of longitudinal frame 130. Internal portions 134c, 134d may be inserted through first and second openings 132a, 132b or through the opening on the monitor facing side of longitudinal frame 130. In some embodiments, internal portions 134c, 134d are inserted through the opening on the monitor facing side of longitudinal frame 130 and include one or more circumferential ridges provided to retain internal portions 134c, 134d by abutting with an internal surface of longitudinal frame 130. The circumferential ridges do not permit insertion of internal portions 134c, 134d through first and second openings 132a, 132b in the first and second ends 131a, 131b.

Returning to FIGS. 8a-b and 9, a monitor cradle 180 is sized and configured to receive monitor 20. Monitor cradle 180 includes a hanger 182 connected to the longitudinal frame and extending downwardly therefrom, a bottom wall 190 connected to the hanger and extending forwardly therefrom, and a front wall 194 extending upwardly from the bottom wall. The bottom wall has a bottom surface 192 configured to the shapes of the first and second sides of the monitor. A curved surface 193 is contiguous with bottom surface 192 and curved to match the curvature of the rounded first edge and the rounded second edge so that the monitor can be positioned in the cradle in the first orientation or the second orientation.

As described above, heat sink 70 of monitor 20 includes centering structure 87 comprising two vertical walls defining cavity 88. Cavity 88 is sized to receive centering protrusion 168 extending from monitor facing side 160. Centering protrusion 168 extends between latches 166 and 170 to facilitate latching of the monitor onto the monitor support bracket.

As shown, hanger 182 is affixed to monitor facing side 160 of longitudinal frame 130. On the opposite side of monitor facing side 160 longitudinal frame 130 is affixed to articulating link 106. A wall opening on monitor facing side 160 may be provided in longitudinal frame 130 to provide access to the latching mechanism (e.g. spring, internal portion, latches), and potentially to enable securement of vertically articulating link 106 to a rear wall of longitudinal frame 130. Longitudinal frame 130 and monitor cradle 180 may be molded from polymeric materials.

In a variation of the present embodiment, longitudinal frame 130 is formed together with hanger 182. For example, hanger 182 may be molded with monitor facing side 160.

Figure 12A:
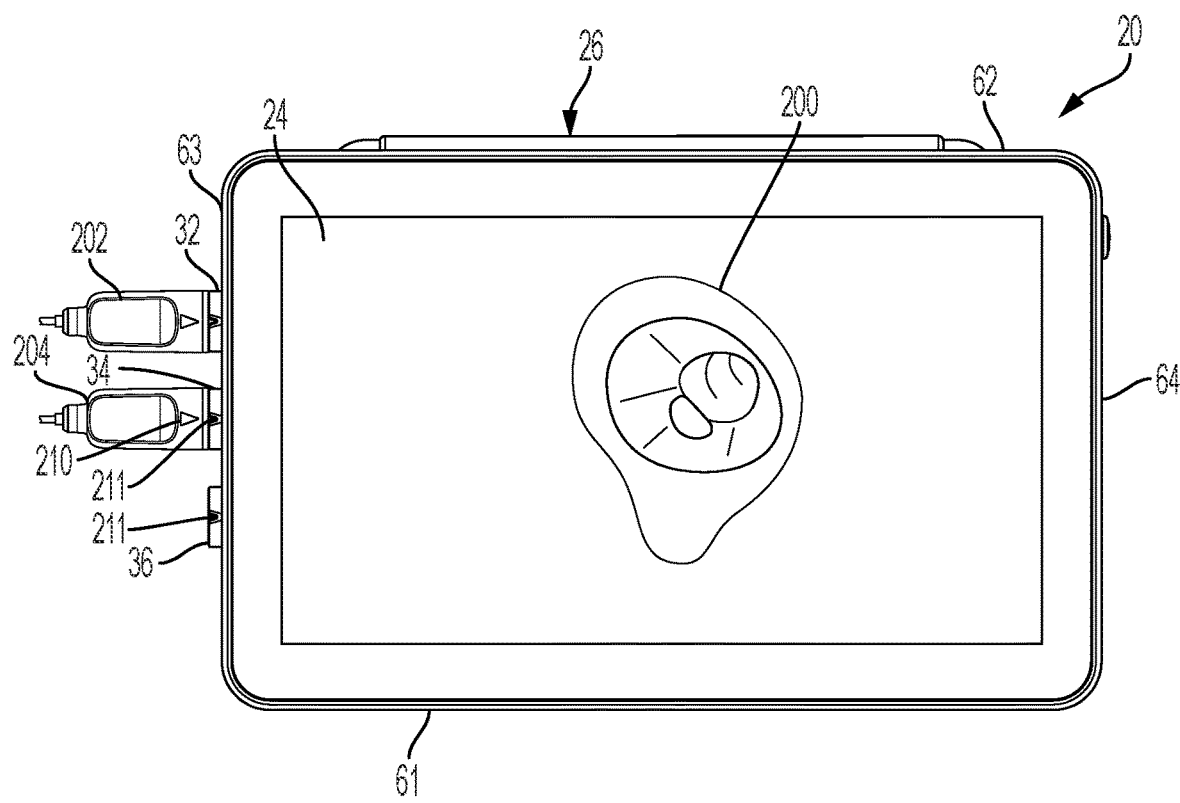
FIGS. 12a and 12b are views of the portable medical monitor of FIG. 1b in a first orientation and a second orientation.
Figure 12B:
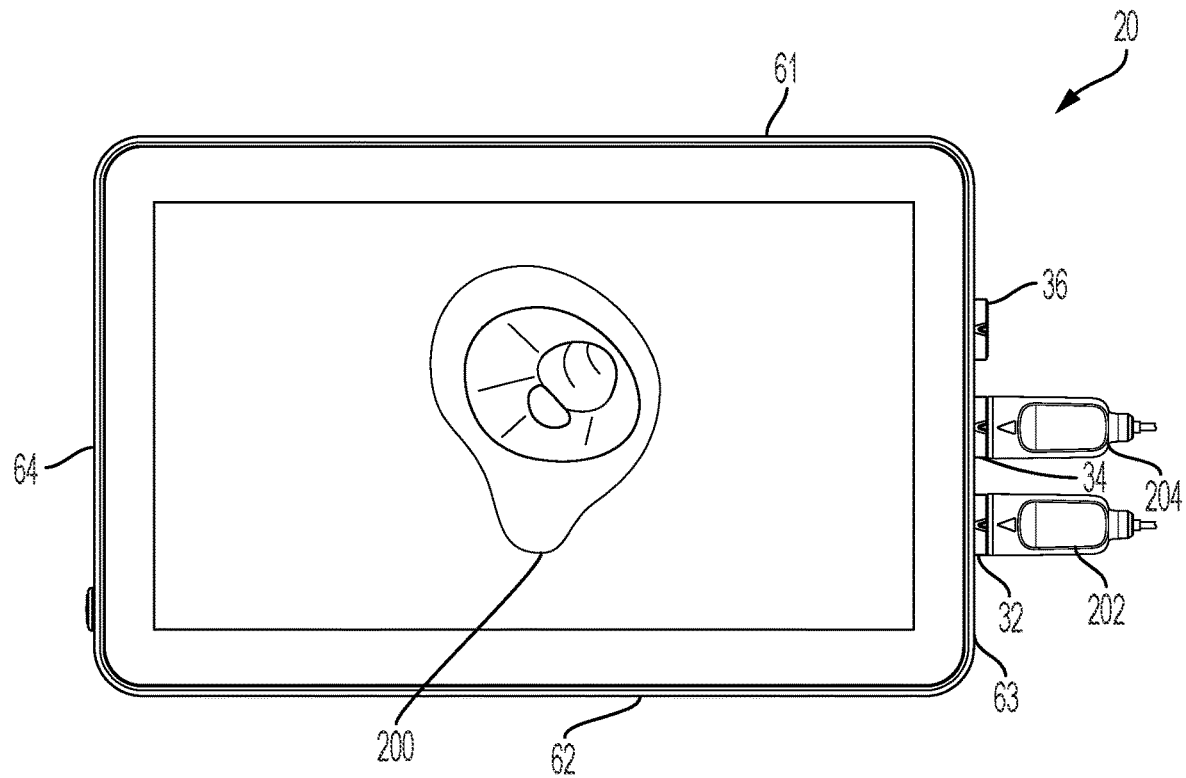

FIGS. 12a and 12b illustrate monitor 20 positioned in the first, or default, orientation (FIG. 12a) and in the second, or inverted, orientation (FIG. 12b), in both cases with connector ports 32, 34, 36 extending from third side 63. A graphical image 200 corresponding to an optical image captured by the image sensor of a videoscope is presented with display module 24. The orientation of the monitor does not change the orientation of the graphical image because the monitor senses the change in orientation and rotates the graphical image in a corresponding manner. Of course, in an alternative embodiment, connector ports 32, 34, 36 can be positioned to extend from fourth side 64.

Cable connectors 202 and 204 are shown inserted into, respectively, connector ports 32 and 34. Cable connector 202 is attached to a cable of a videoscope and cable connector 204 is attached to a cable of another videoscope, as described further with reference to FIG. 23. In some embodiments, each cable connector and matching connector port has a visual technology indicator to ensure the technology of the videoscope is compatible with the technology of the respective connector port.

In some embodiments, alignment indicators 210, 211, visual and tactile, are also provided to facilitate connection of the cable connector with the connector port. The connector port may include communication lines and power conductors to provide power to energize the image sensor of the respective videoscope. The visual technology indicators and alignment indicators are described in additional detail with reference to FIGS. 15 to 17.

In some embodiments, each cable connector and matching connector port has a visual technology indicator and alignment indicators.

Figure 13A:
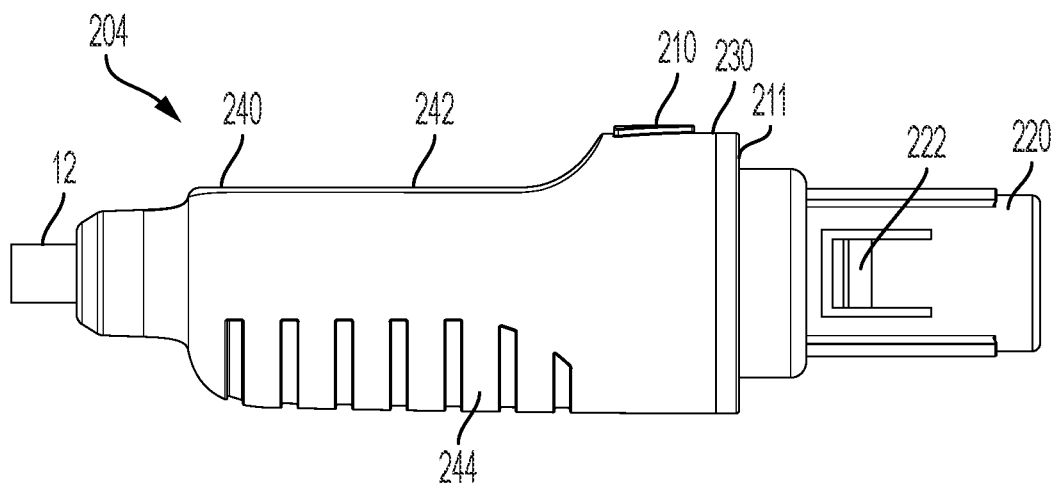
FIGS. 13a, 13b, and 13c are side views of an embodiment of a cable connector of a videoscope operable with the portable medical monitor of FIG. 1b.
Figure 13B:
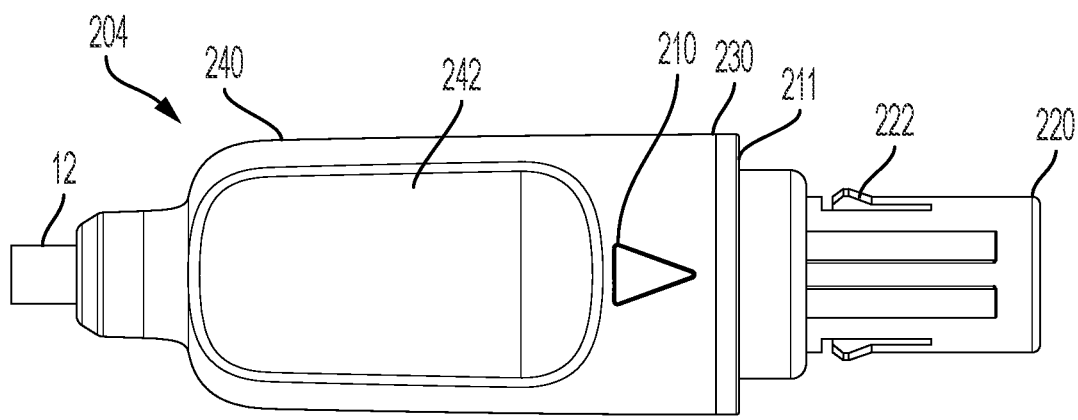
Figure 13C:
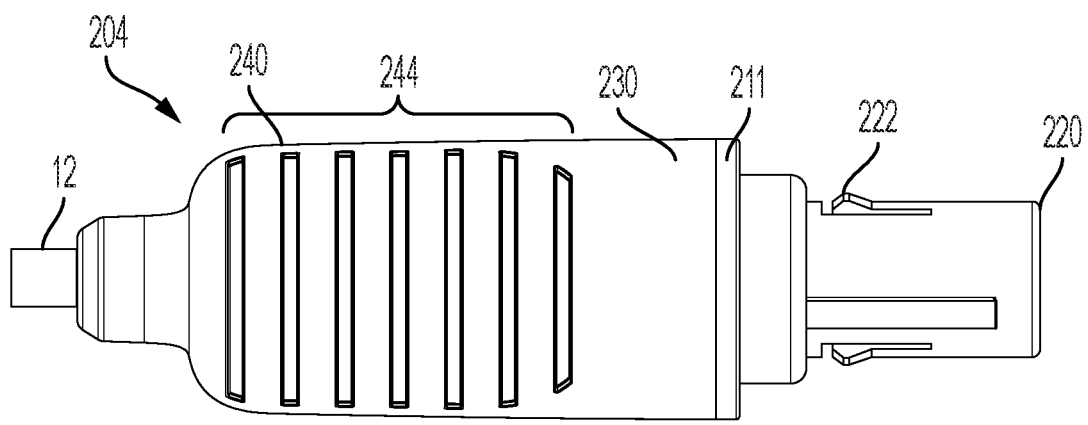

Cable connectors may comprise standard cable connectors or may include technology and/or alignment indicators as shown in FIGS. 13a, 13b, and 13c, which illustrate features of cable connector 204. The features are the same in cable connector 202. Cable connector 204 includes a connection section 220, a middle section 230, and a grip section 240. Middle section 230 is positioned between connection section 220 and grip section 240. Cable 12 extends from grip Connection section 220 includes opposing tabs 222 provided to mate with corresponding recesses and retain cable connector 204 in place once inserted into a connector port. Middle section 230 comprises a visual alignment indicator 210, illustratively a triangle, and a visual technology indicator 230, illustratively a color-coded ring. Visual alignment indicator 210 and visual technology indicator 230 may have the same color. The cross-section of middle section 230 is substantially circular. Grip section 240 comprises tactile orientation indicators 242 and 244. Tactile alignment indicator 242, illustratively a flat surface, enables a user to place its thumb on the surface, and thereby feel the orientation of the cable connector and be able to align it with the monitor's connector ports. Tactile orientation indicator 244, illustratively a textured surface, also allows the user to feel the texture to determine, without looking, how to hold cable connector 202 in the proper orientation relative to the monitor to thereby align the cable connector with the connector ports. As shown, the textured surface comprises a plurality of parallel grooves.

Up to this point several features of monitor 20 were described, including support features pertaining to the orientation of the monitor, and features pertaing to cable connectors and connector ports. Several components of monitor 20 can be characterized as being part of a video processing apparatus (VPA) 520, described in additional detail with reference to FIGS. 22-24, which may but does not require the same support features because it does not include a display module. Therefore, video processing apparatus 520 includes the components of monitor 20 related to communication and manipulation of image data but not necessarily a handle or latching structure, although the handle and/or latching structure may be provided for covenience of the user. Accordingly, monitor 20 is a particular embodiment of video processing apparatus 520.

Figure 14A:
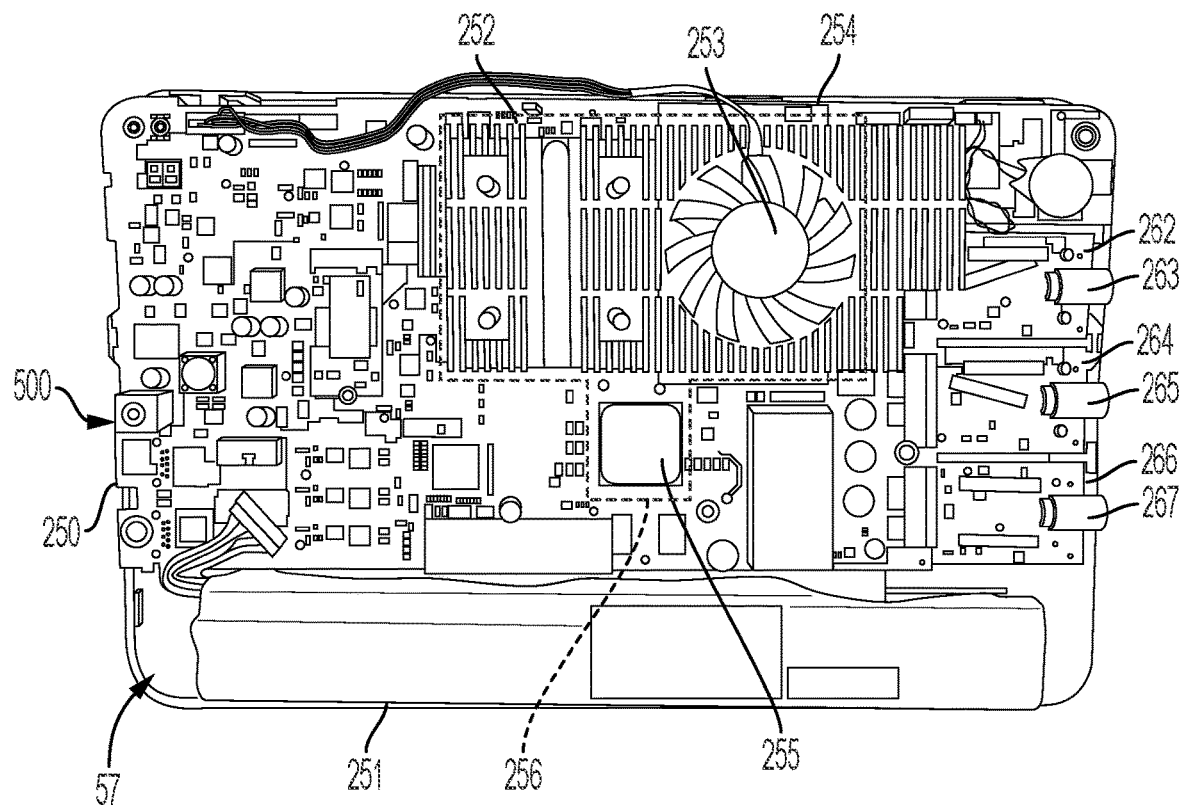
Figure 14B:
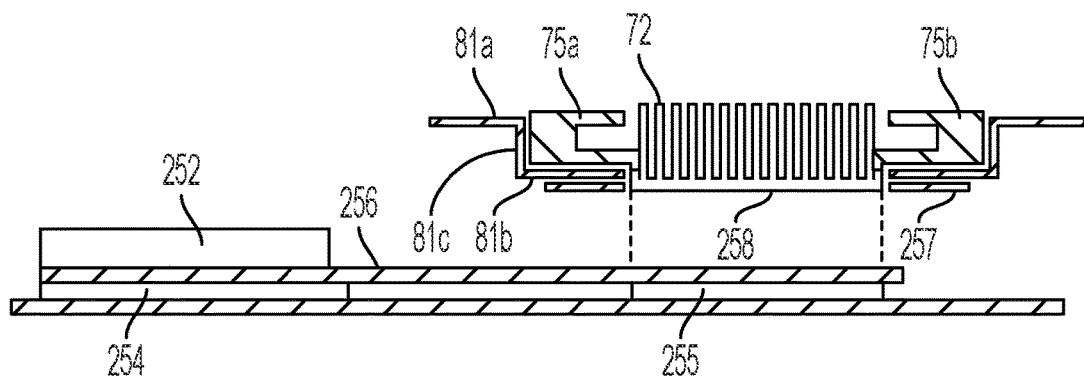

Referring to FIGS. 14a and 14b, components of monitor 20 are depicted which may also be comprised by video processing apparatus 520. These components may include a circuit board 250 and, mounted on circuit board 250, an internal heat sink 252 thermally coupled to a first heat generator circuit 254, a battery 251, a second heat generator circuit 255, and a heat transfer bridge 256 thermally coupling internal heat sink 252 with external heat sink 70. Heat transfer bridge 256 may comprise a sheet of copper physically attached to internal heat sink 252 with external heat sink 70. As shown, heat transfer bridge 256 comprises a first portion positioned between internal heat sink 252 and the first heat generator circuit 254, which may be a memory (see memory 512 in FIG. 22), and a second portion positioned between external heat sink 70 and the second heat generator circuit, which may be an FPGA (see FPGA 514 in FIG. 22). In another example, the first portion of heat transfer bridge 256 is sized and shaped to match, and is attached to, the finned surface of internal heat sink 252 instead of being positioned between internal heat sink 252 and the first heat generator circuit 254. A fan 253 circulates air through the fins of heat sink 252. Hot air may exit the internal space via ventilation grid 80. The heat generator circuits may comprise the FPGA, a processor or central processing unit, a video graphics integrated circuit, and any other circuit integrated in a single semiconductor package and capable to processing a large number of instructions and thus generate heat. A heat generator circuit may also comprise a power regulator and/or power converter, including a DC-DC converter. A surface 258 of heat sink 70 contacts heat transfer bridge 256 which in turn contacts second heat generator circuit 255. Thermally conductive paste or a layer of thermally conductive material may be placed between the heat generators and the heat sinks to improve thermal transfer, as is well known in the art. A plate 257 is placed on the inside of the back wall of the housing. Plate 257 has a through-hole, matching the location of through-hole 91, through which surface 258 is accessible. Plate 257 also provides support to mount heat sink 70 since fasteners 76 pass through heat sink recess wall 81b and are secured within the internal space of the housing through plate 257.

In a variation of the present embodiment, fan 253 is omitted and the internal space is passively cooled by transferring some of the heat produced by the first heat generator circuit through the heat transfer bridge to the external heat sink, where the heat is dissipated. A portion of the heat is also ventilated through the ventilation grid.

In another variation of the present embodiment, fan 253 is provided and the heat transfer bridge is omitted.

In another variation of the present embodiment, only an external heat sink is provided.

Monitor 20 and video processing apparatus 520 comprise one or more connector port. The connector port may include a flexible plug hood, as described below. The flexible plug hood extends from a side of the housing of monitor 20 or video processing apparatus 520. The flexible plug hood may, but does not have to, include an alignment indicator and/or a technology indicator.

Figure 15:
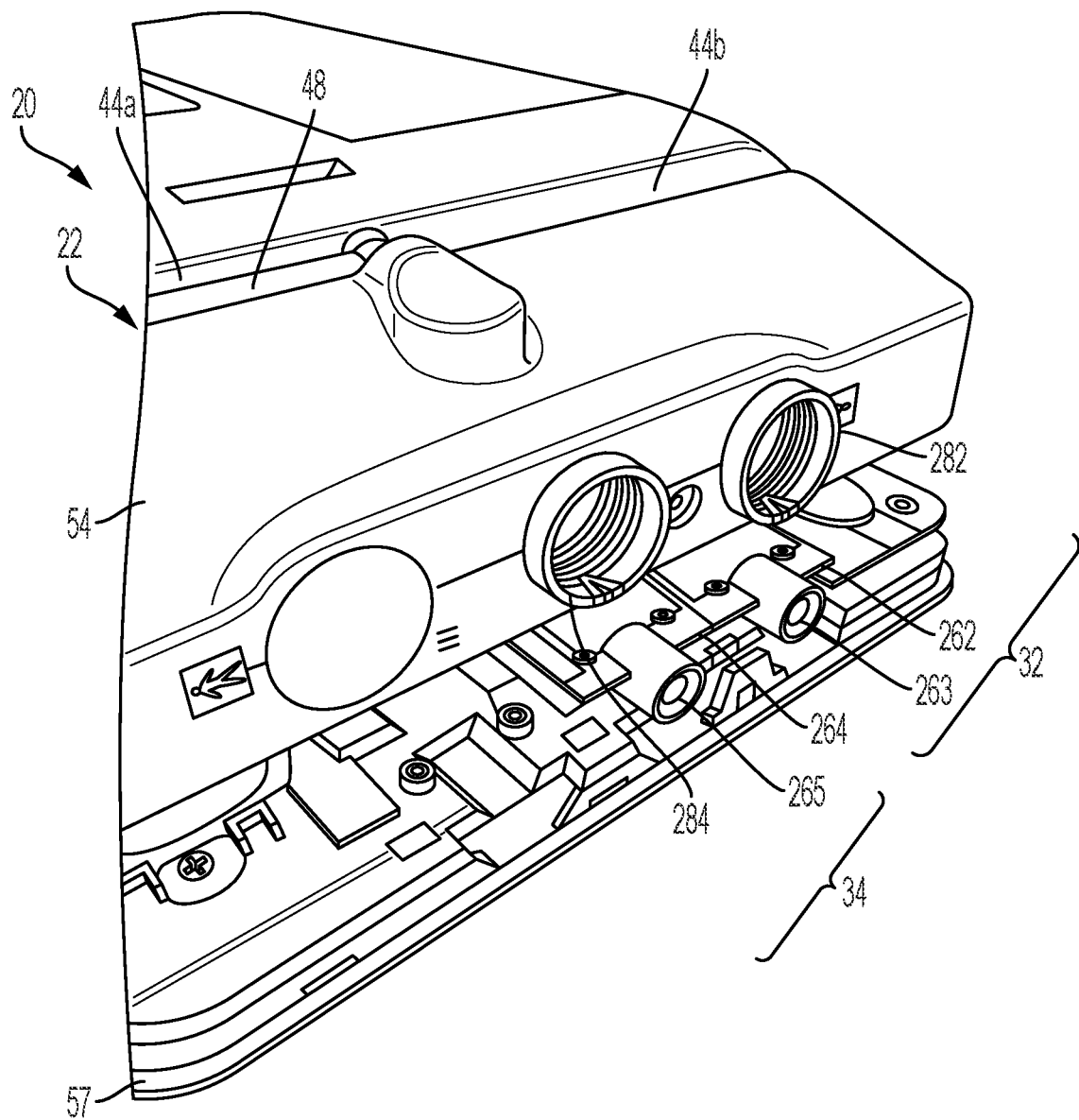
FIG. 15 is a perspective view of the portable medical monitor of FIG. 1b in a partially disassembled state.
Figure 16A:
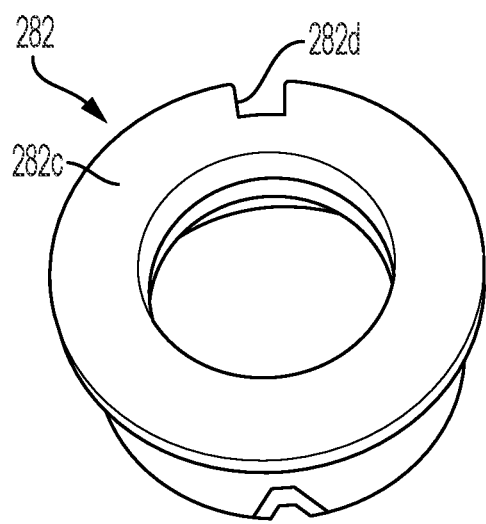
FIGS. 16a, 16b, and 16c are perspective views of an embodiment of a connector ring of the portable medical monitor of FIG. 1b.
Figure 16B:
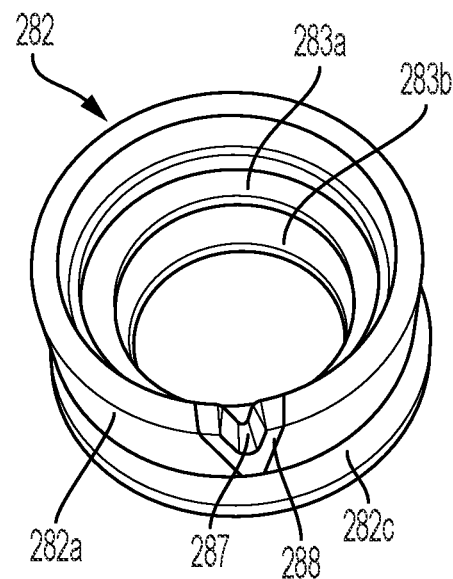
Figure 16C:
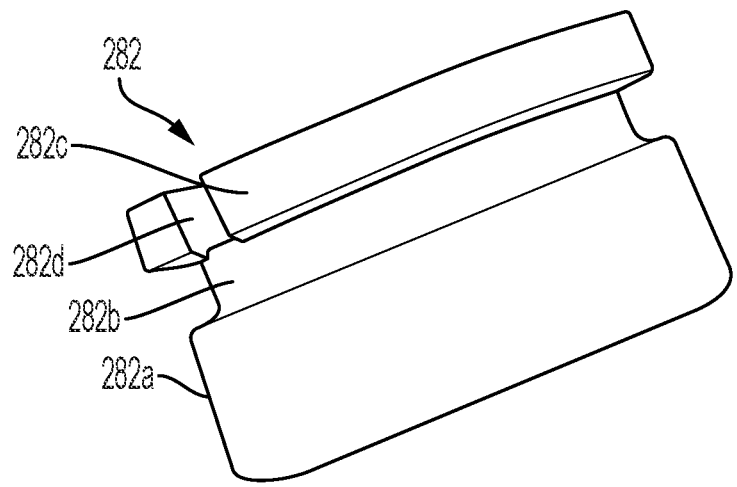
Figure 17:
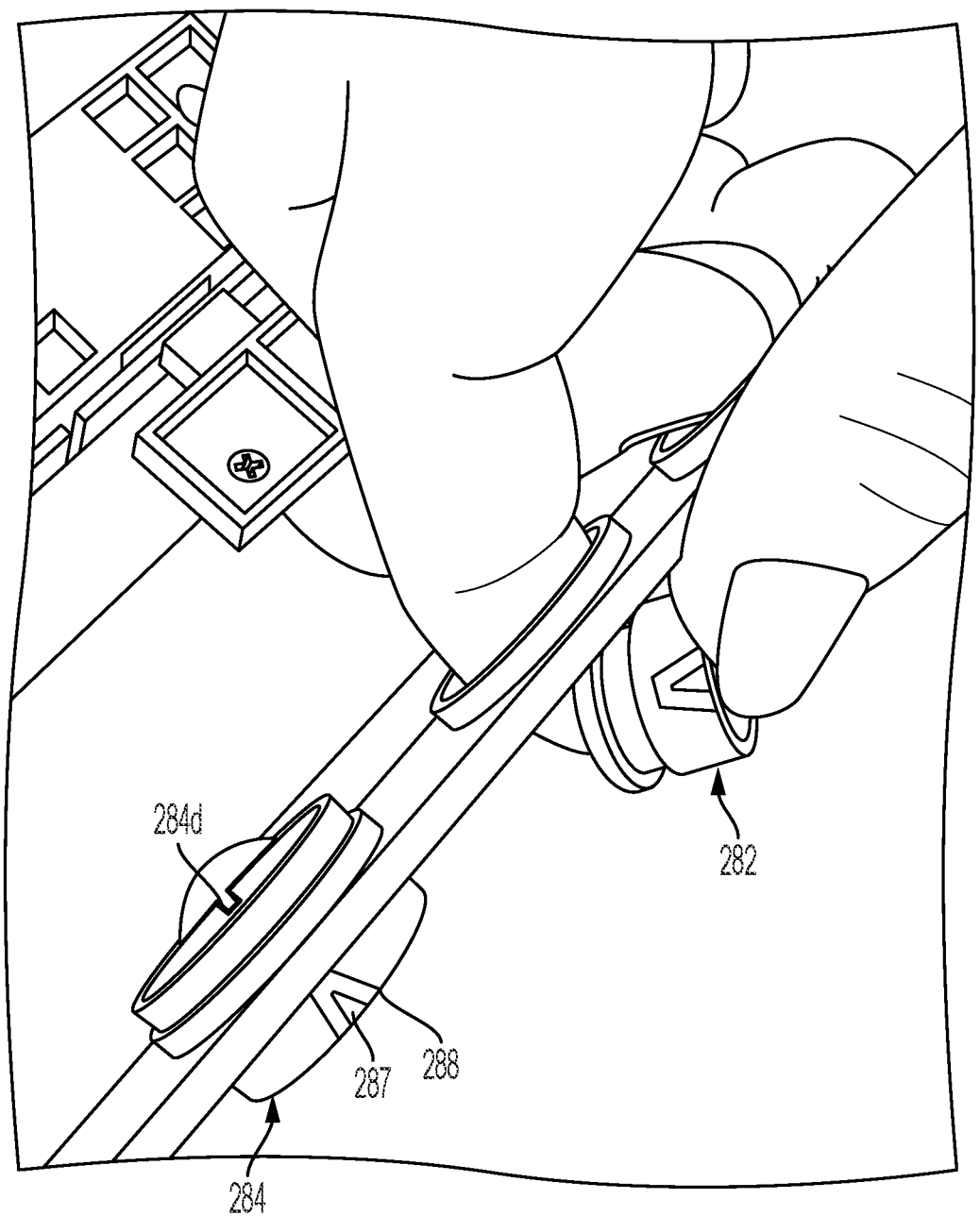
FIG. 17 is a perspective view of the connector ring of FIGS. 16a-c in the process of removal from the housing of the portable medical monitor.

Referring to FIGS. 15-17, each connector port 32, 34, 36 includes a connector 263, 265 mounted on a medical device interface 262, 264. Connectors 263 and 265 are shown mounted on, respectively, medical device interfaces 262 and 264, and more specifically on a circuit board of each medical device interface. The medical device interfaces are removable. Each connector port 32, 34, 36 also includes a connector ring 282, 284 which, in the present embodiment, is associated with the technology of the respective medical device interface. The technology for receiving and outputting image data and for outputting power for the image sensor, lighting device, and other components of a respective videoscope can vary based on the purpose or procedure for which the videoscope is designed, the image sensor model, etc. The videoscopes may be single-use videoscopes, in which case the monitor may be the most expensive component of the video system. Providing removable medical device interfaces and providing technology indicators in the connector port and videoscope cable connectors enables use of different videoscope technologies with the same monitor and updating of the medical device interfaces to match additional or newer versions of videoscopes as they become available, therefore allowing an owner of the monitor to extend its effectiveness and useful life and to increase its value.

Referring to FIGS. 16a-16c and 17, connector ring 282 comprises a plug hood 282a, an intermediate portion 282b, and a retention portion 282d including an alignment cavity 282d. The connector ring mounted on an opening in a wall of the housing. The retention portion and the plug hood are larger in cross-section than the opening in the wall of the housing in at least one radial extent, and the intermediate portion is smaller in cross-section than the opening in the wall of the housing in the at least one extent, therefore the flexible material of the connector ring can be bent to pass the connector ring through the opening until the intermediate portion traverses the opening, at which time the plug hood and the retention portion secure the connector ring in the opening. In another example the retention portion may be threaded to secure the connector ring to a threaded opening in the housing, while still including a flexible plug hood.

As shown, alignment cavity 282d is a notch that fits over a protrusion inside the housing. The protrusion and alignment cavity cause connector ring 282 to fit within an aperture on the side of the monitor with the alignment indicator 287 in the correct radial orientation. Plug hood 282a includes alignment indicator 287, which may be, as shown, a notch shaped as the letter V. At least plug hood 282a is made from a flexible material. In the present embodiment, the connector ring is made from the flexible material, for example silicone or an elastomeric polymer. The connector ring may be molded or machined. Flexibility facilitates insertion of the cable connector, or plug, through the plug hood into the connector of the medical device interface. Additionally, flexibility prevents damage to the plug hood in case the monitor or VMM is accidentally dropped or hit. Thus, because the plug hood will not be damaged by contact, it can extend further than prior art plug hoods. Additionally, flexibility facilitates "blind" (by feel, without looking) insertion of a cable connector through plug hood 282a for coupling with a connector 263, 265. Altogether, the tactile and visual alignment indicators facilitate visual and blind connections, as desired, which can be made more quickly than without the indicators.

The notch of alignment indicator 287 may be surrounded by a frame 288 of material of a color different than the color of the remainder of the connector ring to highlight the position of the notch. For example, frame 288 may be white while connector ring 282 may be blue, green, or another color.

Figure 18:
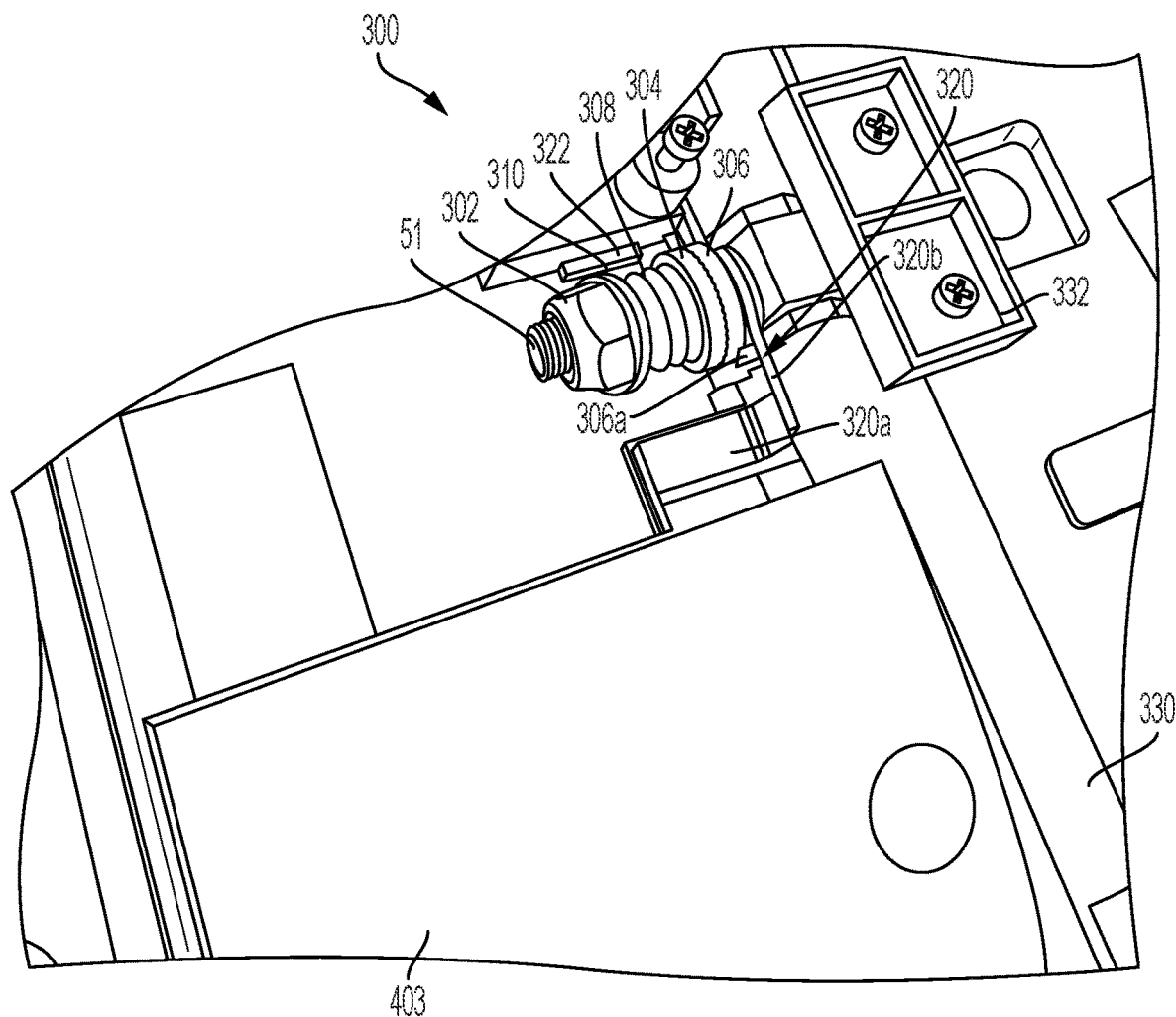
FIGS. 18 and 19 are perspective and diagramatic views of an embodiment of a handle position brake of the portable medical monitor of FIG. 1b.
Figure 19:
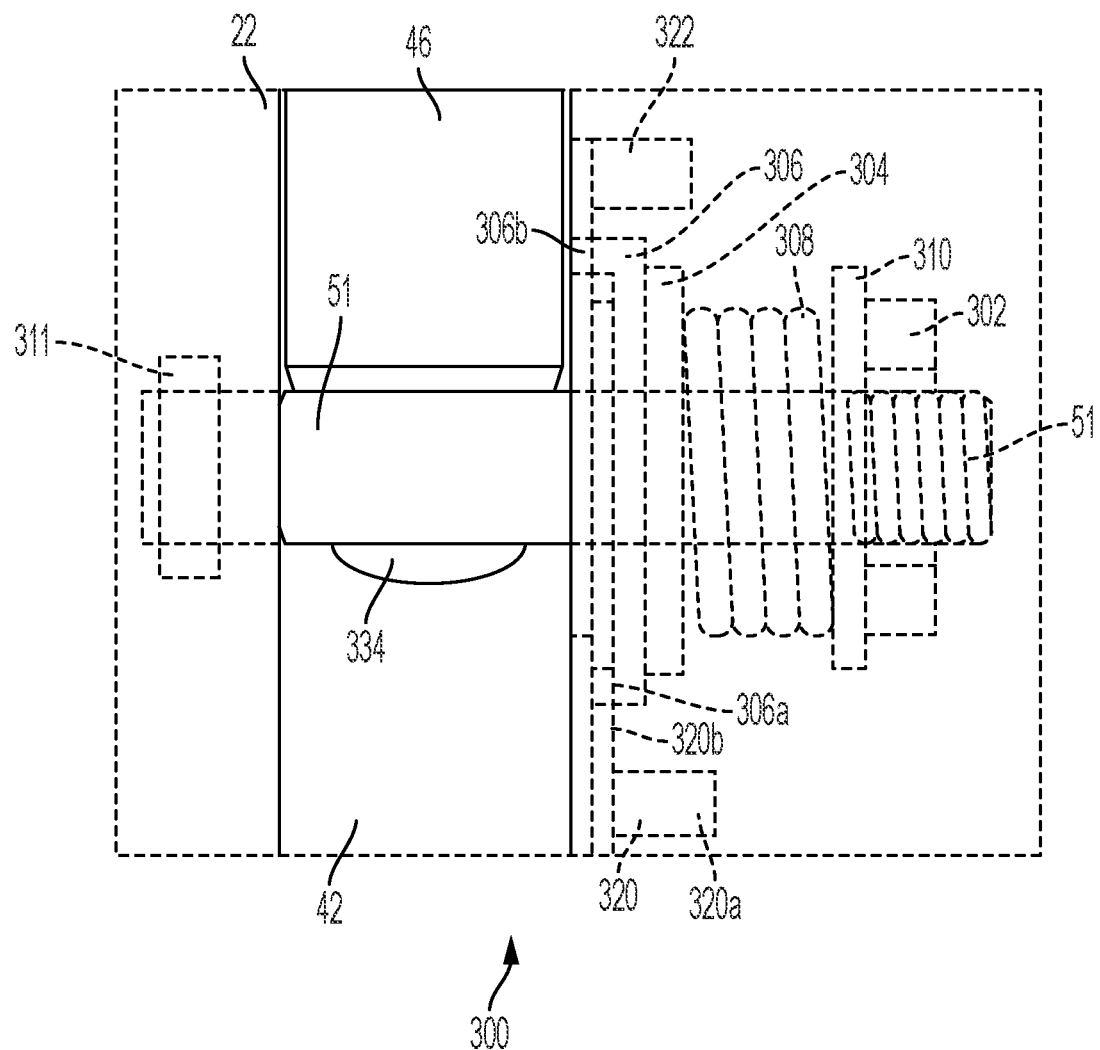

Turning attention now to the handle of monitor 20, as described with reference to FIGS. 2a-5c, the handle can be maintained in one of many positions by a handle position brake. Referring now to FIGS. 18 and 19, the monitor includes a handle position brake on each side. FIG. 18 illustrates an embodiment of a handle position brake 300 viewed from inside housing 22 and therefore showing the internal surface of the wall portion forming groove 42, denoted by numeral 330 in FIG. 18. Handle position brake 300 includes a threaded nut 302 secured to handle axle 51, a first disk 304, a second disk 306, and a spring 308 between threaded nut 302 and first disk 304, spring 308 causing a surface of the first disk to press against a surface of the second disk to create a braking force to maintain handle 26 in one of the plurality of positions as described above. An additional disk 310 is shown between spring 308 and threaded nut 302. The surface of the first disk can be grooved and the surface of the second disk can also be grooved to increase the braking force relative to ungrooved, or flat, disk surfaces. Grooves provide one form of texturing. Other textures may be applied to increase friction between the disk's surfaces. The grooves can be distributed evenly radially, for example every 10-20 degrees, so that protrusions between each pair of grooves can fit in grooves of the opposing disk to provide a discrete position. Thus, for example, if the grooves are spaced 15 degrees apart, the brakes will have different handle positions at 15 degree intervals.

Second disk 306 comprises two keys protruding parallel to handle axle 51. One key penetrates an aperture of a right-hand rotation stop 320 and the other penetrates an aperture of a left-hand rotation stop 322. Each rotation stop comprises a circular portion through which handle axle 51 passes and extending from the circular portion a first arm perpendicular to handle axle 51 and a second arm extending therefrom in parallel to handle axle 51. The rotation stops prevent rotation of second disk 306.

A reinforcement block 332 is affixed to housing 22 on the opposite side of which handle position brake 300 is mounted. A portion of reinforcement block 332 extends over wall 330 and between wall 330 and left-hand rotation stop 322 to reinforce wall 330.

FIG. 19 depicts an external view of a portion of monitor 22 overlapping handle position brake 300. A distal end of handle axle 51 opposite threaded nut 302 has a through-hole. The first end of arm 46 fits in the through-hole and is secured therein by a screw 334. Thus, pivoting movement of arm 46 causes handle axle 51 to pivot only when the friction between the surfaces of the first and second disks 304 and 306 is overcome by the force applied to arm 46. Otherwise, the friction holds arm 46 in its position. A distal end of the handle axle may be supported by a bushing 311.

In some variations of the present embodiment, monitor 20 does not include a handle or a handle position brake.

In some variations of the present embodiment, monitor 20 includes a handle and a handle position brake, and the handle is not pivotally coupled to the housing of the monitor at a middle section thereof Turning attention now to the video output by monitor 20 or video processing apparatus 520, a video output housing recess facilitates connection of video cables while retaining the connectors of the video cable substantially within the recess to enhance retention and prevent accidental disconnection thereof. Referring to FIGS. 20a, 20b, and 20c, video output housing recess 400 is formed by lateral walls 401, 402, 404 and 405, and a bottom wall 403 having an external surface 403a and an internal surface 403b. Connectors 420a, 420b, and 420c are accessible through wall 402. Bottom wall 403 is disposed at an angle beta which is at least 4 degrees relative to the surface of the display screen. Preferably, beta is at least and including 5-25 degrees, and even more preferably beta is at least and including 6-25 degrees. Connector 420a, for example an HDMI connector, is also aligned at angle beta. Connector 420a is mounted on a video output board 410. Optionally, video output board 410 is also supported inside housing 22 at angle beta. A video plug 421 is shown in FIG. 20c plugged into output connector 420a. Advantageously, aligning the connector and the bottom wall of the video output housing recess enables a user to more easily connect the plugs with the connectors of the video output board. Optionally, wall 404 is curved to further facilitate manipulation of plugs with the connectors of the video output board. Wall 404 is opposite 402. The connectors can, but do not have to be, video output connectors. Connectors can be for ethernet, coaxial, and other types of cables and the cables can provide bi-directional communications and/or power.

Another feature of monitor 20 or video processing apparatus 520 is a power receptacle assembly. Referring to FIG. 21, a power receptacle assembly 500 comprises a power socket 501 mounted on circuit board 250 and a corresponding hole 502 in the back wall of housing 22. A power cord plug passes through hole 502 to enter power socket 501 and through power socket 501 provides power to the circuits on circuit board 250 and the medical device interfaces. Advantageously, this design requires or causes removal of the power cord plug before the back portion of housing 22 is removed from the front portion to, for example, swap, remove, or add, medical device interfaces, which ensures the circuits are powered down before the back portion of housing 22 is removed to provide access to the medical device interfaces. Additionally, aligning hole 502 with power socket 501 mounted on the circuit board, which can be referred to as a motherboard, eliminates additional cables in the internal space that would be required if, for example, power socket 501 were mounted on a side of the housing.

As described above, monitor 20 is advantageously operable in default and inverted orientations and can be connected to one or more medical devices, which may, but do not have to, be videoscopes. Thus, monitor 20 includes video processing circuits operable to receive image data, present a graphical user interface to allow a user to manipulate image data with a touch screen, and, optionally, output a video signal to allow remote viewing of the images presented with the touch screen.

Variations of monitor 20 can be provided with various features of monitor 20 but including other features. For example, it might not be desirable to provide a touch screen, or it might be desirable to omit a display module altogether. Omission of the display module might be beneficial to take advantage of evolving video display technologies which improve resolution and reduce cost. Provision of exchangeable medical device interfaces allows for adoption of evolving image sensor and videoscope technologies, thus use of existing or future-developed external video displays could allow presentation of higher resolution or otherwise improved video. Use of external video displays could also leverage existing capital investments. Use of wall-mounted video displays could also reduce reliance on IV poles and, generally, clutter.

Figure 22:
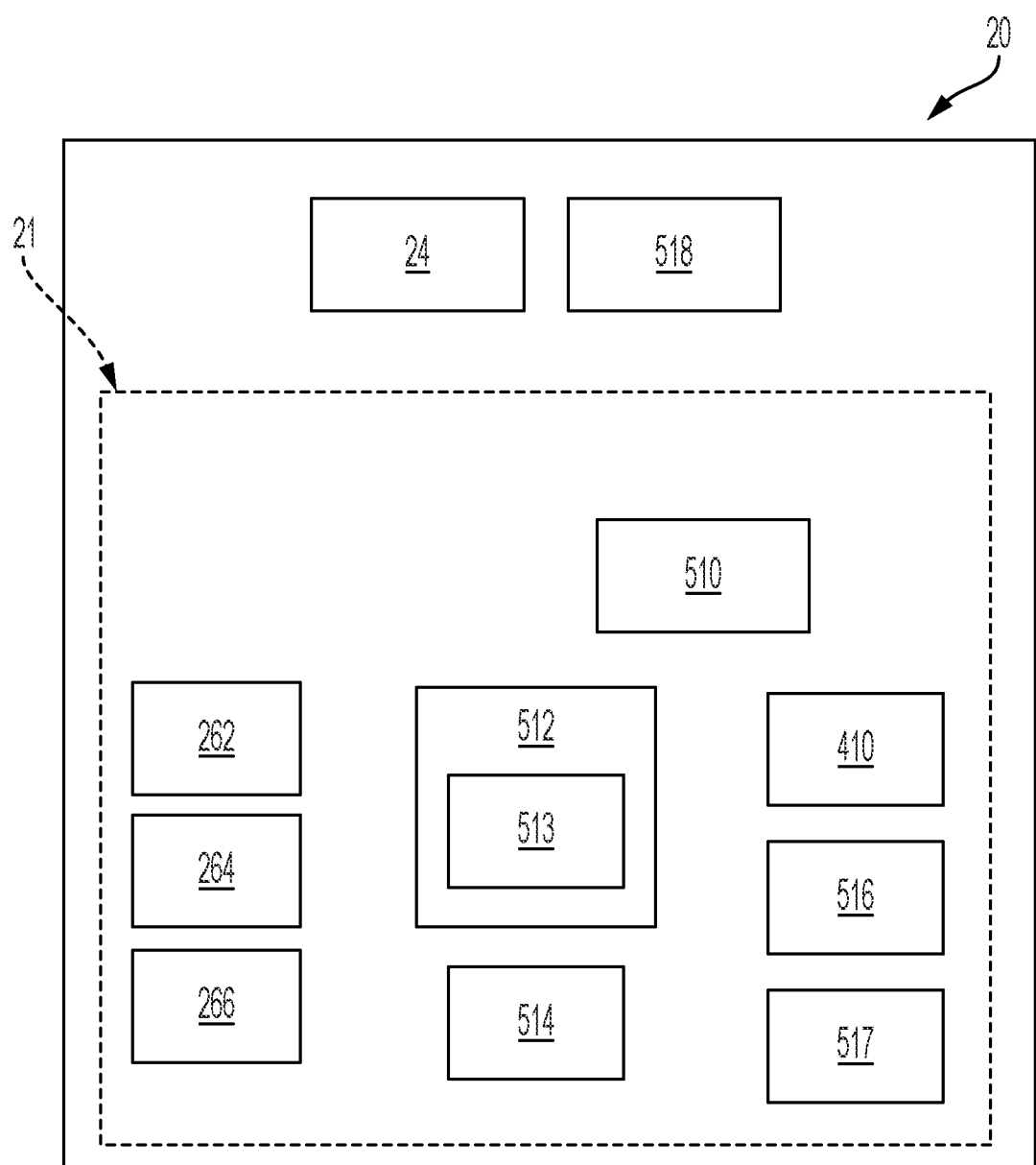
FIG. 22 is a block diagram of an embodiment of portable medical video monitor module.

Video processing circuits and other components will now be described with reference to FIGS. 22-24. FIG. 22 depicts example components of monitor 20. Several components are part of a video monitoring module (VMM) 21. It should be understood that VMM 21 can, but does not have to be, a physical module independent of other components. Instead, VMM 21 is described in terms of its function to simplify description, and the componens that perform the functions can be arranged in any convenient manner. Accordingly, monitor 20 includes VMM 21, display module 24, and, optionally, an orientation sensor 518. The functionality of orientation sensors was described above. VMM 21, display module 24, and an orientation sensor 518 are supported by housing 22, as described above. As shown, VMM 21 includes medical device interfaces 262, 264, and 266. VMM 21 could include fewer medical interfaces and might include a medical device interface that is not removably coupled.

VMM 21 also includes a processor 510, memory 512 including graphical user interface (GUI) logic 513, a field-programmable gate array (FPGA) 514, video output board 410, a user interface 516, and a microphone 517. User interface 516 may comprise a wireless interface operable to receive user inputs via a mouse, keyboard, or other physical user input devices. Example wireless interfaces include Bluetooth and Zigbee controllers. User interface 516 may also comprise a USB port to receive a USB connector including the wireless interface or a USB connector of a wired user input device. Thus, VMM 21 provides for flexibility in receiving user inputs via various user input devices, regardless whether a display module is integrated therewith.

FPGA 514 is optionally provided because it is capable of rapid power-up (i.e. short boot-up time) and thus is useful in emergency situations. FPGAs may also be provided in the medical device interfaces for the same reasons. FPGAs process data very fast compared to other memory/instruction combinations and are re-programmable. Therefore FPGAs facilitate presentation of a live view of the images captured by the videoscope in real-time with minimal latency so that the physician observing the live view can take immediate actions even in emergency situations. As technology evolves, the functionality of FPGA 514 may be combined with processor 510. VMM 21 is therefore not limited to the precise packaged integrated circuits described with reference to FIG. 22 but can be constructed to take advantage of design and cost targets and future video processing technologies. For example, faster/more costly memory may be used to increase graphics processing speed. Graphics processing may be provided in the FPGA or a processor that incorporates graphics processing logic may be used instead.

Figure 23:
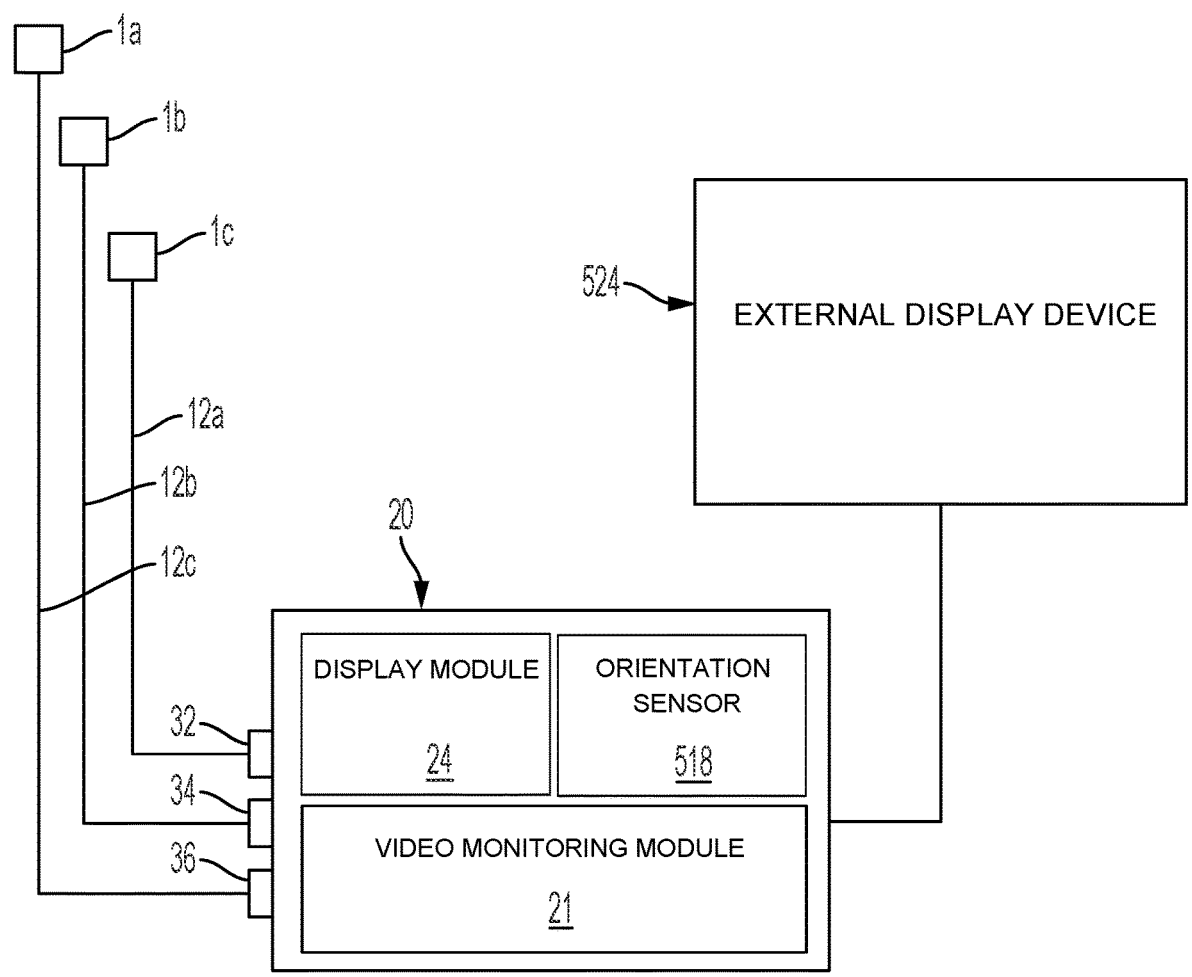
FIG. 23 is a block diagram of an embodiment of the portable medical video monitor of FIG. 1b connected to three videoscopes and an external video display.

FIG. 23 illustrates a system including monitor 20 and three videoscopes 1a, 1b, 1c communicatively coupled to monitor 20 via cables 12a, 12b, and 12c. The videoscopes may comprise, for example, an endotracheal tube with an image sensor at the distal end thereof, a video laryngoscope, an endoscope, a duodenoscope, a colonoscope, an ENT scope, and any other medical device adapted for insertion into a living body and having an image sensor to capture views of body tissues. An external display device 524 is communicatively coupled to monitor 20, for example via video output board 410 and an HDMI cable.

Figure 24:
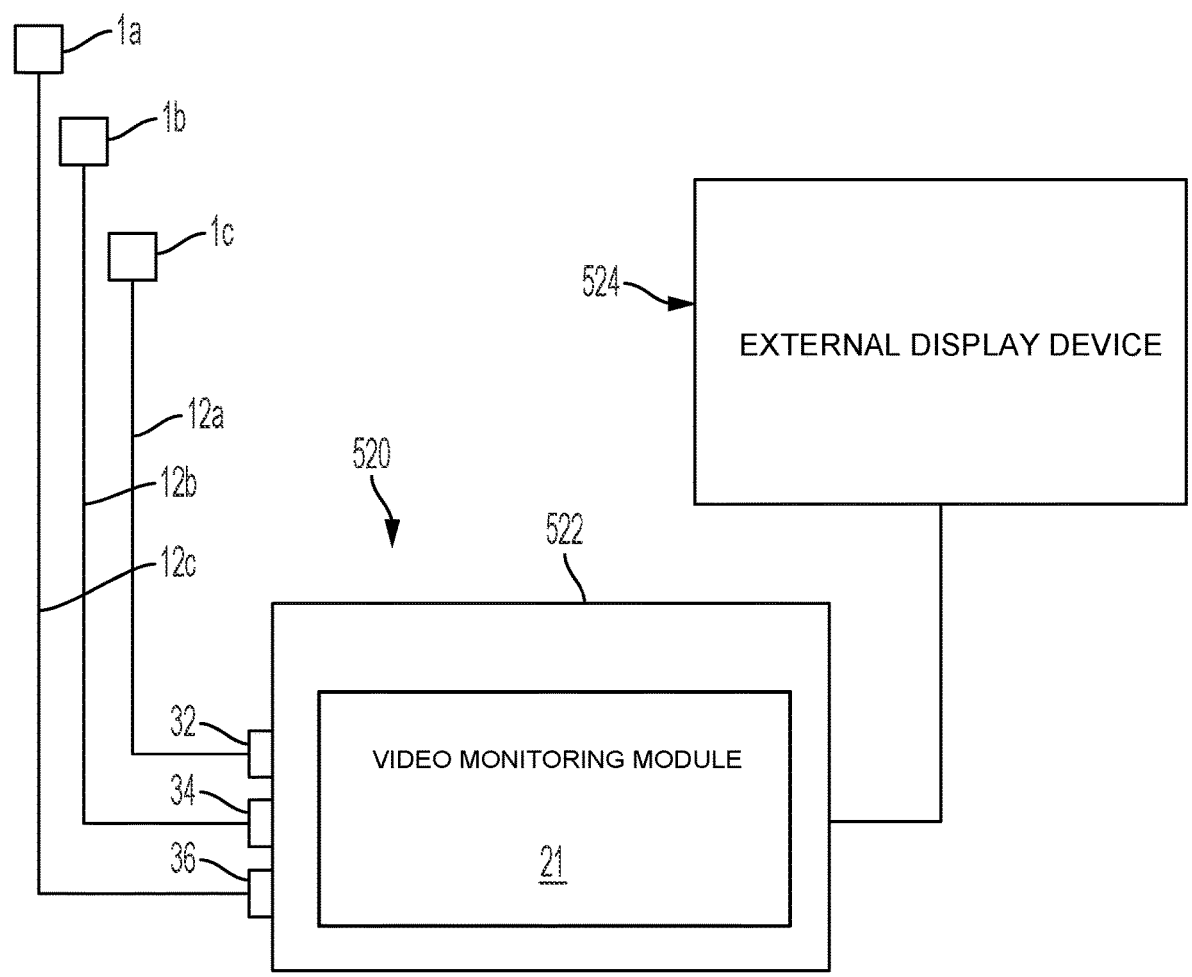
FIG. 24 is a block diagram of another embodiment of a portable medical video monitor connected to three videoscopes and an external video display.

FIG. 24 illustrates a system including a video processing apparatus 520 including a housing 522, VMM 21, and ports 32, 34, and 36. As described above, more or less ports can be included. Video processing apparatus 520 is communicatively coupled to external display device 524. The connector port(s) may include a flexible plug hood, as described above. The flexible plug hood may extends from a side of housing 522. Any of the above-described connector port configurations may be used, including those comprising various indicators technology and orientation indicators.

In some embodiments, VPA 520 is devoid of a display module.

In some embodiments, VPA 520 is devoid of a handle pivotally attached to the back wall of the housing and of grooves sized and shaped to receive the arms of the handle.

In some embodiments, VPA 520 includes the internal and external heat sinks. In some variations of the present embodiment VPA 520 includes the heat transfer bridge. In other variations VPA 520 excludes the heat transfer bridge.

In some embodiments, VPA 520 includes the flexible connector hoods. In some variations of the present embodiments, VPA 520 includes the technology and orientation indicators referred to above. In some variations of the present embodiments, VPA 520 the connector hoods are unmarked by technology and orientation indicators.

The term "logic" as used in this patent application includes software and/or firmware executing on one or more programmable processing devices, application-specific integrated circuits, field-programmable gate arrays, digital signal processors, hardwired logic, or combinations thereof. Therefore, in accordance with the embodiments, various logic may be implemented in any appropriate fashion and would remain in accordance with the embodiments herein disclosed. Logic may comprise processing instructions embedded in non-transitory machine-readable media (e.g. memory).

GUI logic 513 comprises processing instructions to generate a GUI presented with display module 24 and/or external display device 524. The GUI can be responsive to user inputs received via the touch screen or other user inputs. GUI logic 513 may process an output signal from orientation sensor 518 indicative of an orientation of monitor 20, and to present the GUI in an orientation based on the signal from orientation sensor 518.

Processor 510 receives image data from medical device interfaces 262, 264, and 266 and outputs video signals incorporating the GUI and image data. Image data may be referred to "live images" or "live video" if they are received substantially in real-time from the videoscopes. The video signals may be received by a memory buffer and the buffer may be read by the display module or video output card to present the GUI and images. Techniques for presenting images are well known, including techniques using buffers or mapped memory.

GUI logic 513 may present the GUI depending on the orientation signal from the orientation sensor or a user instruction to invert the view. A view corresponds to the display area of a display screen. The GUI may comprise first and second panels provided side-by-side in the view. The second panel presents live images and is positioned on the right side of the view, with the first panel positioned on the left side of the view. Even when the monitor orientation changes, the first panel remains on the left of the second panel.

The GUI may present in the first panel a small version of live images provided by a second videoscope and the user may use the GUI to switch the live images from the first and second videoscopes so that the images from the second videoscope are presented in the second panel while the images from the first videoscope are reduced and presented in the first panel. The last videoscope connected to a connector port may be shown in the second panel by default. However the views from the different videoscopes can selected by the user with the GUI for presentation in the first or second panel or not displayed at all.

The GUI may present various icons corresponding to actions selectable by the user with any of the above-described user input devices, to for example store a copy of a live image, store a portion of video corresponding to live images, invert the views, apply correction curves to the image data to reduce overexposure, etc.

Additional examples within the scope of the disclosure are listed below.

Support Bracket Examples:

1. A support bracket for a portable monitor, the support bracket comprising:
   a longitudinal frame having a first end opposite a second end, a first opening in the first end and a second opening in the second end, the longitudinal frame also including a monitor facing wall having at least one opening between the first end and the second end;
   a first actuator accessible through the first opening and sized and shaped to translate in the first end;
   a second actuator accessible through the second opening and sized and shaped to translate in the second end;
   a first latch extending through the at least one opening and including a slanted surface, the first latch biased to a first position in which the first latch is nearer the first end than in a second position, wherein force applied to the first actuator causes the first actuator to translate the first latch to the second position, and wherein force applied to the slanted surface perpendicularly to the monitor facing wall translates the first latch to the second position;
   a second latch extending through the at least one opening and including a slanted surface, the second latch biased to a first position in which the first latch is nearer the second end than in a second position, wherein force applied to the second actuator causes the second actuator to translate the second latch to the second position, and wherein force applied to the slanted surface perpendicularly to the monitor facing wall translates the second latch to the second position.

2. The support bracket of example 1, wherein each of the first latch and the second latch includes an internal portion disposed within the longitudinal frame.

3. The support bracket of example 2, wherein the internal portion of the first latch is connected to the first actuator and the internal portion of the second latch is connected to the second actuator.

4. The support bracket of any one of examples 1 to 3, further comprising a spring connected to the internal portion of the first latch to bias the first latch to the first position.

5. The support bracket of example 1, further comprising a hanger connected to the longitudinal frame and extending downwardly therefrom, a bottom wall connected to the hanger, and a front wall extending upwardly from the bottom wall, wherein the hanger, the bottom wall, and the front wall define a cradle sized and shaped to receive the portable monitor.

6. The support bracket of example 5, wherein the hanger has a top portion including a first opening and a second opening, wherein the at least one opening is sized and shaped to receive the top portion of the hanger, and wherein the first latch extends through the first opening and the second latch extends through the second opening when the hanger is attached to the longitudinal frame.

7. The support bracket of example 6, wherein the top portion of the hanger includes a centering protrusion positioned between the first opening and the second opening.

8. A support bracket and monitor arrangement, comprising:
the support bracket of any one of examples 1 to 7; and
a monitor operable in a first orientation and a second orientation, the monitor comprising a display, a housing supporting the display, and a latching structure including a first latch retainer, a first recess, a second latch retainer, and a second recess,
wherein the first latch retainer is sized and shaped to apply force upon the slanted surface of the first latch when the monitor is moved toward the support bracket to move the first latch from the first position to the second position and to retain the first latch once the first latch is received by the first recess and returns to the first position, and
wherein the second latch retainer is sized and shaped to apply force upon the slanted surface of the second latch when the monitor is moved toward the support bracket to move the second latch from the first position to the second position and to retain the second latch once the second latch is received by the second recess and returns to the first position.

9. The support bracket and portable monitor arrangement of example 8, wherein the monitor comprises an external heat sink and the external heat sink includes the latching structure.

10. The support bracket and portable monitor arrangement of any one of examples 8 and 9, wherein the monitor comprises a handle having arms, handle axles connected to the arms to pivotally connect the handle to the housing, the handle axles defining a rotation axis, and wherein the latching structure is on a plane perpendicular to the display and traversing the rotation axis.

11. The support bracket and portable monitor arrangement of any one of examples 8 to 10, wherein the monitor has a first side opposite a second side, wherein in the first orientation the first side is below the second side, wherein the monitor has a third side opposite a fourth side, a distance from the third side to the fourth side defining a length of the monitor, wherein a length of the longitudinal frame is at least 65% of the length of the portable monitor.

12. The support bracket and portable monitor arrangement of any one of examples 8 to 10, wherein the monitor has a first lateral side and a second, opposite, lateral side, wherein a length of the longitudinal frame is sufficient to enable a user holding the monitor with the right and left hands positioned on the first lateral side and the second lateral side to apply force to the first actuator and the second actuator with the left hand and the right hand to release the monitor from the support bracket.

13. The support bracket and portable monitor arrangement of any one of examples 8 to 10, wherein the monitor has a first side opposite a second side, wherein in the first orientation the first side is below the second side, a distance from the first side to the second side defining a width of the monitor, wherein a distance from a plane bisecting the first latch horizontally to the bottom wall is substantially equal to ½ of the width of the monitor.

14. The support bracket and portable monitor arrangement of any one of examples 8 to 10, wherein the monitor has a first side opposite a second side, wherein in the first orientation the first side is below the second side, wherein the cradle is sized and shaped to permit latching of the latching structure onto the first latch and the second latch with the monitor supported by the cradle, in the first orientation and also with the monitor in the second orientation.

15. The support bracket and portable monitor arrangement of any one of the preceding examples, the monitor further comprising a circuit board mounted inside the housing and a power socket mounted on the circuit board and sized and shaped to receive therein a power plug, wherein the housing includes a front portion removably attached to a back portion, the back portion including a through-hole aligned with the power socket, the through-hole sized and shaped to receive therethrough the power plug, wherein removal of the back portion removes the power plug from the power socket.

16. The support bracket and portable monitor arrangement of any one of the preceding examples, the monitor further comprising an internal heat sink within the internal space defined by the housing, and an external heat sink mounted on an outer surface of the housing.

17. The support bracket and portable monitor arrangement of example 16, the monitor further comprising a heat transfer bridge thermally connecting the internal heat sink and the external heat sink.

18. The support bracket and portable monitor arrangement of example 17, wherein the monitor is devoid of an internal fan.

19. A support bracket and video processing apparatus (VPA) arrangement, comprising:
the support bracket of any one of examples 1 to 7; and
a VPA comprising a housing and a latching structure including a first latch retainer, a first recess, a second latch retainer, and a second recess,
wherein the first latch retainer is sized and shaped to apply force upon the slanted surface of the first latch when the VPA is moved toward the support bracket to move the first latch from the first position to the second position and to retain the first latch once the first latch is received by the first recess and returns to the first position, and
wherein the second latch retainer is sized and shaped to apply force upon the slanted surface of the second latch when the VPA is moved toward the support bracket to move the second latch from the first position to the second position and to retain the second latch once the second latch is received by the second recess and returns to the first position.

20. The support bracket and VPA arrangement of example 19, wherein the VPA comprises an external heat sink and the external heat sink includes the latching structure.

21. The support bracket and VPA arrangement of any one of examples 19 or 20, wherein the VPA has a first lateral side and a second, opposite, lateral side, wherein a length of the longitudinal frame is sufficient to enable a user holding the VPA with the right and left hands positioned on the first lateral side and the second lateral side to apply force to the first actuator and the second actuator with the left hand and the right hand to release the VPA from the support bracket.

22. The support bracket and VPA arrangement of any one of examples 19 to 21, wherein the VPA has a first side opposite a second side, wherein in the first orientation the first side is below the second side, a distance from the first side to the second side defining a width of the VPA, wherein a distance from a plane bisecting the first latch horizontally to the bottom wall is substantially equal to ½ of the width of the VPA.

23. The support bracket and VPA arrangement of any one of the preceding examples, the VPA further comprising a circuit board mounted inside the housing and a power socket mounted on the circuit board and sized and shaped to receive therein a power plug, wherein the housing includes a front portion removably attached to a back portion, the back portion including a through-hole aligned with the power socket, the through-hole sized and shaped to receive therethrough the power plug, wherein removal of the back portion removes the power plug from the power socket.

24. The support bracket and VPA arrangement of any one of the preceding examples, the PVA further comprising an internal heat sink within the internal space defined by the housing, and an external heat sink mounted on an outer surface of the housing.

25. The support bracket and VPA arrangement of example 24, the VPA further comprising a heat transfer bridge thermally connecting the internal heat sink and the external heat sink.

26. The support bracket and VPA arrangement of any one of the preceding examples, wherein the PVA is devoid of an internal fan.

27. The support bracket and VPA arrangement of any one of examples 19 to 26, wherein the VPA is devoid of a display module.

28. The support bracket and VPA arrangement of any one of examples 19 to 26, wherein the VPA is devoid of a handle pivotally attached to the back wall.

Connector Ring Examples:

1. A connector ring for a video processing apparatus (VPA), the connector ring comprising:
   a retention portion;
   an intermediate portion; and
   a plug hood made of a flexible material, the intermediate portion connecting the retention portion to the plug hood,
   wherein the retention portion and the plug hood are larger in cross-section than the intermediate portion in at least one radial extent.

2. The connector ring of example 1, wherein the plug hood comprises a visual technology indicator associated with a technology of a medical device interface of the VPA and a plug alignment indicator, wherein the retention portion includes an alignment feature corresponding with the alignment indicator.

3. The connector ring of examples 1 or 2, wherein the plug hood comprises a cylindrical wall including the visual technology indicator and the plug alignment indicator.

4. The connector ring of examples 1, 2, or 3, wherein the visual technology indicator comprises a color associated with the technology of the medical device interface, and the plug alignment indicator comprises a notch in the cylindrical wall, and wherein the plug hood further comprises an alignment indicia of a color different than the color associated with the technology of the medical device interface.

5. The connector ring of any one of examples 1-4, wherein the retention portion of the connector ring comprises an arcuate wall including the alignment feature, and the alignment feature is sized and shaped to radially align the connector ring with a medical device connector of the medical device interface of the VPA.

6. The connector ring of any one of examples 1-5, wherein the alignment feature comprises an opening in the arcuate wall.

7. The connector ring of any one of examples 1-6, wherein the flexible material is selected to adopt a bent state under application of force and an unbent state upon release of the force, and wherein the connector hood consists substantially of the flexible material.

8. The connector ring of any one of examples 1-7, wherein the VPA comprises a housing and a display module supported by the housing and including a display screen.

9. A video processing apparatus (VPA), comprising:
   a housing defining an interior space of the VPA and including a wall having an opening;
   a medical device interface including a medical device connector axially aligned with the opening on the wall of the housing; and
   a connector ring as in any one of examples 1-8.

10. The VPA of example 9, wherein the connector ring comprises a retention portion located in the interior space and radially aligned with the medical device connector, an intermediate portion traversing the opening, and a plug hood made of flexible material and extending outwardly from the intermediate portion, wherein the retention portion and the plug hood are larger in cross-section than the opening in the wall of the housing in at least one radial extent, and wherein the intermediate portion is smaller in cross-section than the opening in the wall of the housing in the at least one extent.

11. The VPA of example 10, wherein the retention portion of the connector ring comprises an arcuate wall including an alignment feature sized and shaped to radially align the connector ring with the medical device connector.

12. The VPA of example 11, wherein the alignment feature comprises a notch in the arcuate wall.

13. The VPA of example 11, wherein the plug hood of the connector ring comprises a visual technology indicator.

14. The VPA of example 10, wherein the plug hood of the connector ring comprises a plug alignment indicator.

15. The VPA of example 14, wherein the plug hood comprises a cylindrical wall and the plug alignment indicator comprises a notch in the cylindrical wall.

16. The VPA of example 9, wherein the plug hood comprises a cylindrical wall and the plug alignment indicator comprises a notch in the cylindrical wall.

17. The VPA of example 9, wherein the plug hood of the connector ring comprises a cylindrical wall including a visual technology indicator and a plug alignment indicator.

18. The VPA of example 17, wherein the visual technology indicator comprises a color associated with a technology of the medical device interface, and the plug alignment indicator comprises a notch in the cylindrical wall, and wherein the plug hood further comprises an alignment indicia of a color different than the color associated with the technology of the medical device interface.

19. The VPA of any one of examples 8-18, wherein the VPA further comprises a display module supported by the housing and including a display screen.

20. A method of assemblying a video processing apparatus (VPA), comprising:
   providing a housing including a wall having an opening;
   removably connecting a medical device interface to a circuit board located in an internal space of the VPA, the medical device interface including a connector axially aligned with the opening on the wall of the housing when the medical device interface is connected to the circuit board;
   providing a connector ring including a retention portion, an intermediate portion, and a plug hood, the intermediate portion connecting the retention portion to the plug hood, the connector ring having a flexible portion capable of adopting a bent state and an unbent state, in the unbent state the flexible portion having a cross-section larger than the opening and thus not being insertable through the opening, and in the bent state the flexible portion having a cross-section smaller than the opening and thus being insertable through the opening;

bending the flexible portion into the bent state;

while in the bent state, inserting the portion of the connector ring through the opening until the opening surrounds the intermediate portion; and releasing the connector ring to allow the flexible portion to adopt the unbent state.

21. The method of example 20, further comprising radially aligning the connector ring with the connector of the medical device interface.

22. The method of example 20, wherein the connector hood comprises the flexible portion.

23. The method of example 20, wherein the flexible portion comprises a flexible polymeric material selected to adopt the bent state and the unbent state, and wherein the connector hood consists substantially of the flexible polymeric material.

24. The method of any one of examples 20 to 23, wherein the VPA comprises a display module supported by the housing and including a display screen.

Indicator Examples:

1. A video processing apparatus (VPA) comprising:
a housing defining an interior space of the VPA;
a first medical device interface located in the interior space and including a connector adapted to removably connect a cable associated with first medical device having an image sensor;
a first visual technology indicator corresponding to the first medical device interface and positioned adjacent the first medical device interface; and
a second medical device interface located in the interior space and including a second connector adapted to removably connect a cable associated with a second medical device having an image sensor, the second medical device interface being operably different than the first medical device interface;
a second visual technology indicator corresponding to the second medical device interface and positioned adjacent the second medical device interface,
wherein the first technology indicator is different from the second technology indicator to thereby facilitate connection of the first medical device with the first medical device interface and of the second medical device with the second medical device interface.

2. The VPA of example 1, wherein the first medical device interface is located adjacent the second medical device interface.

3. The VPA of example 1, wherein the housing comprises a first opening and the first visual technology indicator comprises or is comprised by a ring removably positioned in the first opening, and wherein the housing comprises a second opening and the second visual technology indicator comprises or is comprised by a ring removably positioned in the second opening.

4. The VPA of example 3, wherein the first opening is permanently aligned with the first interface socket and the second opening is permanently aligned with the second interface socket.

5. The VPA of example 4, wherein the first visual technology indicator can be moved from the first opening to the second opening and the first medical device interface can be moved from the first interface socket to the second interface socket.

6. The VPA of example 3, wherein the ring corresponding to the first visual technology indicator surrounds the connector of the first medical device interface.

7. The VPA of example 3, wherein the first visual technology indicator comprises a first color and the second visual technology indicator comprises a second color different than the first color, to thereby color-code the first medical device interface and the second medical device interface.

8. The VPA of only one of examples 1 to 7, further comprising a first interface socket and a second interface socket, the first interface socket and the second interface socket sized and shaped to removably and interchangeably receive the first medical device interface and the second medical device interface.

9. The VPA of example 8, wherein the first interface socket and the second interface socket are identical.

10. The VPA of example 1, wherein the first visual technology indicator is comprised by the first connector and the second visual technology indicator is comprised by the second connector.

11. The VPA of any one of examples 1 to 10, wherein the VPA further comprises a display module supported by the housing and including a display screen.

12. The VPA of any one of the preceding examples, further comprising a circuit board mounted inside the housing and a power socket mounted on the circuit board and sized and shaped to receive therein a power plug, wherein the housing includes a front portion removably attached to a back portion, the back portion including a through-hole aligned with the power socket, the through-hole sized and shaped to receive therethrough the power plug, wherein removal of the back portion removes the power plug from the power socket.

13. The VPA of any one of the preceding examples, further comprising an internal heat sink within the internal space defined by the housing, and an external heat sink mounted on an outer surface of the housing.

14. The VPA of example 3, further comprising a heat transfer bridge thermally connecting the internal heat sink and the external heat sink.

15. The VPA of example 14, wherein the VPA is devoid of an internal fan.

16. A visualization system comprising:
the VPA of any one of examples 1 to 15;
the first medical device, the first medical device including a connector plug including a first visual indicator corresponding to the first visual technology indicator; and
the second medical device, the second medical device including a connector plug having a second visual indicator corresponding to the second visual technology indicator.

16. The visualization system of example 16, wherein the first visual technology indicator and the first visual indicator comprise a first color, and wherein the second visual technology indicator and the second visual indicator comprise a second color different than the first color, to thereby color-code the first medical device with the first medical device interface and the second medical device with the second medical device interface.

17. A method of making a video processing apparatus (VPA), comprising:
providing a housing having a first opening adjacent a second opening;
providing a motherboard including a first interface socket and a second interface socket, the first interface socket sized and shaped as the second interface socket, the first interface socket aligned with the first opening when the VPA is assembled, and the second interface socket aligned with the second opening when the VPA is assembled;

removably connecting a first medical device interface to the first interface socket, the first medical device interface adapted to removably connect a first medical device having an image sensor;

removably connecting a second medical device interface to the second interface socket, the second medical device interface adapted to removably connect a second medical device having an image sensor, the second medical device being different than the first medical device;

removably positioning a first ring comprising a first visual technology indicator in the first opening; and removably positioning a second ring comprising a second visual technology indicator in the second opening, the second visual technology indicator being different than the first visual technology indicator, wherein the first technology indicator is different from the second technology indicator to thereby facilitate connection of a first medical device with the first medical device interface and of a second medical device with the second medical device interface.

Support Features Examples:

1. A portable monitor operable in a first orientation and a second orientation, the monitor comprising:
a display module;
a housing supporting the display module, the housing having a first side and a second side opposite the first side, a third side and a fourth side opposite the third side and orthogonal to the first side, and a back side opposite the display module, wherein in the first orientation the first side is below the second side and, and wherein in the second orientation the first side is above the second side; and
a handle having arms and a bar extending between the arms,
wherein the back side of the housing includes a middle section extending between the third side and the fourth side equidistantly between the first side and the second side, the middle section having a height less than 4.0 centimeters, and
wherein each of the arms has a first end pivotally attached to the middle section of the housing and a second end opposite the first end and connected to the bar.

2. The monitor of example 1, wherein the middle section has a height less than 3.0 centimeters.

3. The monitor of example 1, wherein a center plane bisects the housing in equal parts, and wherein the handle axles comprise rotation axes lying in the center plane.

4. The monitor of any one of examples 1 to 3, wherein the housing comprises a rounded first edge connecting the first side to the back side and a rounded second edge connecting the second side to the back side, wherein the bar of the handle is operable to support the monitor at an angle to a horizontal plane ranging at least between 15-75 degrees, permitting the monitor to rest on the rounded first edge in the first orientation and on the rounded second edge in the second orientation.

5. The monitor of any one of examples 1 to 4, wherein the back side of the housing includes grooves sized and shaped to receive, respectively, the arms of the handle.

6. The monitor of any one of examples 1 to 4, further comprising a handle axle connected to the first end of one of the arms, the handle axle traversing one of the grooves to define a first section of the groove on one side of the handle axle and a second section of the groove on an opposite side of the handle axle, wherein the handle is pivotable about the handle axle to a plurality of positions including a first position, in which the one of the arms is received by the first section of the groove, a second position, in which the one of the arms is received by the second section of the groove, and intermediate positions between the first position and the second position.

7. The monitor of example 6, further including a handle position brake including one of the handle axles, a first disk having a surface including grooves defining protrusions therebetween, and a second disk having a surface including grooves defining protrusions therebetween, wherein the grooves of the first disk are shaped to match the protrusions of the second disk to thereby define the intermediate positions.

8. The monitor of example 6, further including a handle position brake including the handle axle, a first disk, a second disk, and a spring, the handle axle passing through the first disk, the second disk, and the spring, and the spring causing a surface of the first disk to press against a surface of the second disk to create a braking force to maintain the handle in one of the plurality of positions.

9. The monitor of example 8, wherein the surface of at least one of the first disk and the second disk comprises grooves to increase the braking force relative to disk surfaces without grooves.

10. The monitor of examples 7 or 9, wherein the grooves of the first disk extend radially and are evenly distributed.

11. The monitor of example 10, wherein the grooves are evenly distributed at between 5 and 20 degrees from each other.

12. The monitor of any one of the preceding examples, wherein the housing comprises a rounded first edge connecting the first side to the back side and a rounded second edge connecting the second side to the back side, and wherein the rounded first edge has a curvature radius equal to a curvature radius of the rounded second edge.

13. The monitor of example 12, wherein the curvature radius of the rounded first edge is greater than 2.0 centimeters.

14. A portable monitor operable in a first orientation and a second orientation, the monitor comprising:
a display module;
a housing supporting the display module, the housing having a first side and a second side opposite the first side, a third side and a fourth side opposite the third side and orthogonal to the first side, and a back side opposite the display module, wherein in the first orientation the first side is below the second side and, and wherein in the second orientation the first side is above the second side;
a handle having arms, the arms having first ends opposite second ends, and a bar extending between and connected to the second ends of arms; and
handle axles connected to the first ends of the arms to pivotally connect the handle to the housing,
wherein the back side of the housing includes grooves sized and shaped to receive, respectively, the arms of the handle, and
wherein the handle axles traverse, at least partially, the grooves to define first sections of the grooves on one side of the handle axles and second sections of the grooves on opposite sides of the handle axles, wherein the handle is pivotable about the handle axles to a plurality of positions including a first position, in which the arms are received by the first sections of the grooves, a second position, in which the arms are received by the second sections of the grooves, and intermediate positions between the first position and the second position.

15. The monitor of example 14, further including a handle position brake including one of the handle axles, a first disk having a surface including grooves defining protrusions therebetween, and a second disk having a surface including grooves defining protrusions therebetween, wherein the grooves of the first disk are shaped to match the protrusions of the second disk to thereby define the intermediate positions.

16. The monitor of example 15, wherein the grooves of the first disk are evenly distributed at between 5 and 20 degrees.

17. The monitor of any one of examples 14 to 16, wherein the housing comprises a rounded first edge connecting the first side to the back side and a rounded second edge connecting the second side to the back side, and wherein the rounded first edge has a curvature radius equal to a curvature radius of the rounded second edge.

18. The monitor of any one of examples 14 to 17, wherein the monitor has a weight, wherein between 40-60% of the weight is between the handle axles and the first side of the monitor, and wherein between 40-60% of the weight is between the handle axles and the second side of the monitor.

19. A method of using a monitor as in any one of examples 1 to 18, the method comprising:
  placing the monitor in the first orientation on a support structure with the handle in a first of the plurality of intermediate positions;
  pivoting the handle to a second of the plurality of positions; and
  prior to or after pivoting the handle to the second of the plurality of positions, placing the monitor in the second orientation on the support structure.

Video Out Examples:

1. A video processing apparatus (VPA) comprising:
  a housing defining an interior space of the VPA, the housing having a first side and a second side opposite the first side, a third side and a fourth side opposite the third side and orthogonal to the first side, and a back wall opposite the display module, the back wall comprising a main portion laying on a back plane, a recessed portion recessed from the back plane and defining a video connection recess, and a recessed wall extending from the main portion to the recessed portion, the recessed wall having a video connector opening, and the recessed portion having an angled surface lying at an angle of at least 5 degrees relative to the back plane; and
  a video output socket in the interior space and aligned with the video connector opening of the recessed wall, whereby the angled surface facilitates insertion of a video connector into the video output socket.

2. The VPA of example 1, further comprising a video output card, wherein the video output socket is mounted on the video output card.

3. The VPA of example 2, wherein the video output card is supported by the housing parallel to the angled surface of the recessed portion of the back wall.

4. The VPA of any one of examples 1 to 3, wherein the recessed wall extends parallel to the first side.

5. The VPA of example 4, wherein the recessed portion extends from the recessed wall toward the first side of the VPA.

6. The VPA of example 5, wherein a distance from the recessed portion to the back plane decreases in a direction from the recessed wall toward the first side of the VPA.

7. The VPA of example 1, wherein the VPA includes a handle pivotally affixed to the back wall and operable to pivot about a rotation axis, wherein the recessed wall is positioned between the rotation axis and the first side of the VPA.

8. The VPA of example 1, wherein the VPA includes a handle and the main portion of the back wall comprises grooves, the handle including arms having first ends opposite second ends and a bar extending between and connected to the second ends of arms, wherein the grooves are sized and shaped to receive the arms of the handle, wherein the video connection recess is positioned between the grooves.

9. The VPA of example 8, wherein the handle is pivotally affixed to the back wall and operable to pivot about a rotation axis passing through the grooves to define first sections of the grooves on one side of the rotation axis and second sections of the grooves on an opposite side of the rotation axis, wherein the handle is pivotable about the rotation axis to a plurality of positions including a first position, in which the arms are received by the first sections of the grooves, a second position, in which the arms are received by the second sections of the grooves, and intermediate positions between the first position and the second position.

10. The VPA of example 9, wherein the video connection recess is positioned between the second sections of the grooves on the opposite side of the rotation axis.

11. The VPA of example 9, further comprising an external heat sink positioned between the second sections of the grooves on the opposite side of the rotation axis and adjacent the video connection recess.

12. The VPA of any one of examples 8 to 11, wherein the recessed wall extends parallel to the first side of the VPA, and wherein a distance from the recessed portion to the back plane decreases in a direction from the recessed wall toward the first side of the VPA.

13. The VPA of any one of examples 1 to 12, further comprising a display module supported by the housing and including a display screen.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

The scope of the invention is to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

We claim:

1. A medical monitor comprising:
   a display;
   a housing defining an internal space and supporting the display, the housing having a first side opposite a second side and a back wall, the back wall comprising a ventilation grid adjacent the second side, a main portion laying on a back plane, and a heat sink recess recessed from the back plane and adjacent the first side;
   an external heat sink positioned in the heat sink recess and having a heat receiving surface;
   an internal heat sink within the internal space; and
   a heat transfer bridge thermally coupling the internal heat sink and the external heat sink, the heat transfer bridge being a metal component having a first portion opposite a second portion, the first portion sized and shaped to receive heat and the second portion having a heat transfer surface positioned adjacent to and parallel with the heat receiving surface of the external heat sink to transfer the heat to the external heat sink.

2. The medical monitor of claim 1, wherein in a default orientation of the medial monitor the ventilation grid is above the external heat sink.

3. The medical monitor of claim 1, wherein the medical monitor is devoid of a fan.

4. The medical monitor of claim 1, wherein a center plane bisects the housing in equal parts, wherein the ventilation grid is located between the second side and the center plane, and wherein the external heat sink has an external surface, a majority of external surface being located between the center plane and the first side of the housing.

5. The medical monitor of claim 4, wherein the internal heat sink is located between the second side and the center plane.

6. The medical monitor of claim 5, wherein the internal heat sink is located between the display and the ventilation grids overlapping at least a portion of the ventilation grid.

7. The medical monitor of claim 1, wherein the housing further comprises a third side opposite a fourth side and connecting the first side to the second side, the third side of the housing including a first opening and a second opening, and the medical monitor further comprising:
   a first videoscope interface positioned in the internal space and including a first connector axially aligned with the first opening;
   a first connector ring including a retention portion positioned in the internal space, a plug hood outside the internal space, and an intermediate portion traversing the first opening and connecting the plug hood to the retention portion, the plug hood sized and shaped to receive a plug of a first videoscope operable to provide a first video stream to be presented with the display, the plug hood comprised of a flexible material including a first color corresponding to a technology of the first videoscope;
   a second videoscope interface positioned in the internal space and including a second connector axially aligned with the second opening; and
   a second connector ring including a retention portion positioned in the internal space, a plug hood outside the internal space, and an intermediate portion traversing the second opening and connecting the plug hood to the retention portion, the plug hood sized and shaped to receive a plug of a second videoscope operable to provide a second video stream to be presented with the display, the plug hood comprised of a flexible material including a second color corresponding to a technology of the second videoscope which is different in at least one respect from the technology of the first videoscope.

8. The medical monitor of claim 7, wherein the first videoscope interface can be repositioned in the internal space with the first connector axially aligned with the second opening; and wherein the first connector ring can be repositioned with the intermediate portion traversing the second opening, the first color indicating to a user where to couple the first videoscope.

9. The medical monitor of claim 7, wherein the plug hood of the first connector ring comprises a cylindrical shape sized to receive the plug of the first videoscope and having an outer edge and an inner edge, the plug hood further comprising a V-shaped notch extending inwardly from the outer edge without reaching the inner edge.

10. The medical monitor of claim 9, wherein the plug hood of the first connector ring comprises a frame adjacent the V-shaped notch comprising a color different than the first color, and wherein the remainder of the plug hood comprises the first color.

11. The medical monitor of claim 10, wherein the frame comprises the color white and the first color comprises the color blue, the combination of the colors white and blue highlighting a location of the V-shaped notch to facilitate alignment of a plug of the first videoscope.

12. The medical monitor of claim 1, further comprising:
   a handle having arms, the arms having first ends opposite second ends, and a bar extending between and connected to the second ends of arms; and
   handle axles connected to the first ends of the arms to pivotally connect the handle to the housing,
   wherein the back wall of the housing includes grooves sized and shaped to receive, respectively, the arms of the handle, and
   wherein the handle axles traverse, at least partially, the grooves to define first sections of the grooves on one side of the handle axles and second sections of the grooves on opposite sides of the handle axles, wherein the handle is pivotable about the handle axles to a plurality of positions including a first position, in which the arms are received by the first sections of the grooves, a second position, in which the arms are received by the second sections of the grooves, and intermediate positions between the first position and the second position.

13. A visualization system comprising:
   a first videoscope comprising a first technology operable to output a first video stream with a plug including a first color corresponding to the first technology;
   a second videoscope comprising a second technology different front the first technology in at least one respect and operable to output a second video stream with a plug including a second color corresponding to the second technology; and
   a monitor including:
      a display;
      a housing defining an internal space and supporting the display, the housing having a first side opposite a second side and a back wall, the back wall comprising a ventilation grid adjacent the second side, a main portion laying on a back plane, and a heat sink recess recessed from the back plane and adjacent the first side;
      an external heat sink positioned in the heat sink recess;

an internal heat sink within the internal space;
a heat transfer bridge thermally coupling the internal heat sink and the external heat sink;
a first videoscope interface positioned in the internal space and including a first connector;
a second videoscope interface positioned in the internal space concurrently with the first videoscope interface and including a second connector;
a first connector ring including a retention portion positioned in the internal space, a plug hood outside the internal space, and an intermediate portion traversing the first opening and connecting the plug hood to the retention portion, the plug hood sized and shaped to receive the plug of the first videoscope and comprised of a flexible material having the first color; and
a second connector ring including a retention portion positioned in the internal space, a plug hood outside the internal space, and an intermediate portion traversing the second opening and connecting the plug hood to the retention portion, the plug hood sized and shaped to receive the plug of the second videoscope and comprised of a flexible material having the second color.

14. The visualization system of claim 13, wherein the housing further comprises a lateral wall including a first opening and a second opening, wherein the first videoscope interface is positionable in the internal space with the first connector axially aligned with the first opening or with the second opening, and wherein the second videoscope interface is positionable in the internal space with the second connector axially aligned with the other of the first opening or the second opening.

15. The visualization system of claim 13, wherein the plug hood of the first connector ring comprises a cylindrical shape sized to receive the plug of the first videoscope and having an outer edge and an inner edge, the plug hood further comprising a V-shaped notch extending inwardly from the outer edge without reaching the inner edge.

16. The visualization system of claim 15, wherein the plug hood of the first connector ring comprises a frame adjacent the V-shaped notch comprising a color different than the first color, and wherein the remainder of the plug hood comprises the first color.

17. The visualization system of claim 16, wherein the frame comprises the color white and the first color comprises the color blue, the combination of the colors white and blue highlighting a location of the V-shaped notch to facilitate alignment of a plug of the first videoscope.

18. A method of configuring a visualization system, the method comprising:
providing a monitor including:
 a display;
 a housing defining an internal space and supporting the display, the housing having a side wall, a first side opposite a second side and a back wall, the back wall comprising a ventilation grid adjacent the second side, a main portion laying on a back plane, and a heat sink recess recessed from the back plane and adjacent the first side, and the side wall including a first opening and a second opening;
 an external heat sink positioned in the heat sink recess and having a heat receiving surface;
 an internal heat sink within the internal space; and
 a heat transfer bridge thermally coupling the internal heat sink and the external heat sink, the heat transfer bridge being a metal component having a first portion opposite a second portion, the first portion sized and shaped to receive heat and the second portion having a heat transfer surface positioned adjacent to and parallel with the heat receiving surface of the external heat sink to transfer the heat to the external heat sink;
providing a first videoscope interface including a first connector, the first videoscope interface positionable in the internal space with the first connector axially aligned with the first opening or with the second opening; and
providing a second videoscope interface including a second connector, the second videoscope interface positionable in the internal space concurrently with the first videoscope interface and with the second connector axially aligned with the other of the first opening or the second opening.

19. The method of claim 18, further comprising:
positioning the first videoscope interface in the internal space;
positioning a first connector ring in the first opening or the second opening, the first connector ring including a retention portion positioned in the internal space, a plug hood outside the internal space, and an intermediate portion connecting the plug hood to the retention portion;
positioning the second videoscope interface in the internal space;
positioning a second connector ring in the other of the first opening or the second opening, the second connector ring including a retention portion positioned in the internal space, a plug hood outside the internal space, and an intermediate portion connecting the plug hood to the retention portion,
wherein the plug hood of the first connector ring is sized and shaped to receive a plug of a first videoscope and comprised of a flexible material having a first color, and
wherein the plug hood of the second connector ring is sized and shaped to receive a plug of a second videoscope and comprised of a flexible material having a second color, and
wherein the first videoscope and the second videoscope comprise technologies that differ in at least one respect, the first color and the second color corresponding, respectively, to the technology of the first videoscope and the second videoscope.

20. A medical monitor comprising:
a display;
a housing defining an internal space and supporting the display, the housing having a first side opposite a second side and a back wall, the back wall comprising a ventilation grid adjacent the second side, a main portion laying on a back plane, and a heat sink recess recessed from the back plane and adjacent the first side;
an external heat sink positioned in the heat sink recess;
an internal heat sink within the internal space; and
a heat transfer bridge thermally coupling the internal heat sink and the external heat sink,
wherein the housing further comprises a third side opposite a fourth side and connecting the first side to the second side, the third side of the housing including a first opening and a second opening, and the medical monitor further comprising:
a first videoscope interface positioned in the internal space and including a first connector axially aligned with the first opening;

a first connector ring including a retention portion positioned in the internal space, a plug hood outside the internal space, and an intermediate portion traversing the first opening and connecting the plug hood to the retention portion, the plug hood sized and shaped to receive a plug of a first videoscope operable to provide a first video stream to be presented with the display, the plug hood comprised of a flexible material including a first color corresponding to a technology of the first videoscope;

a second videoscope interface positioned in the internal space and including a second connector axially aligned with the second opening; and a second connector ring including a retention portion positioned in the internal space, a plug hood outside the internal space, and an intermediate portion traversing the second opening and connecting the plug hood to the retention portion, the plug hood sized and shaped to receive a plug of a second videoscope operable to provide a second video stream to be presented with the display, the plug hood comprised of a flexible material including a second color corresponding to a technology of the second videoscope which is different in at least one respect from the technology of the first videoscope.

21. The medical monitor of claim 20, wherein the first videoscope interface can be repositioned in the internal space with the first connector axially aligned with the second opening; and wherein the first connector ring can be repositioned with the intermediate portion traversing the second opening, the first color indicating to a user where to couple the first videoscope.

22. The medical monitor of claim 20, wherein the plug hood of the first connector ring comprises a cylindrical shape sized to receive the plug of the first videoscope and having an outer edge and an inner edge, the plug hood further comprising a V-shaped notch extending inwardly from the outer edge without reaching the inner edge.

* * * * *